United States Patent
Kura et al.

(10) Patent No.: US 7,998,058 B2
(45) Date of Patent: Aug. 16, 2011

(54) ENDOSCOPE SYSTEM COMPRISING ENDOSCOPE TO WHICH MEDICAL INSTRUMENT IS ATTACHED

(75) Inventors: Yasuhito Kura, Tokyo (JP); Takehiro Nishiie, Tokyo (JP); Yoshio Onuki, Tokyo (JP); Kazushi Murakami, Tokyo (JP); Takaaki Komiya, Tokyo (JP)

(73) Assignee: Olympus Medical Systems Corporation, Tokyo (JP)

( * ) Notice: Subject to any disclaimer, the term of this patent is extended or adjusted under 35 U.S.C. 154(b) by 1151 days.

(21) Appl. No.: 11/529,016

(22) Filed: Sep. 28, 2006

(65) Prior Publication Data

US 2007/0078301 A1    Apr. 5, 2007

(30) Foreign Application Priority Data

Sep. 28, 2005    (JP) .................................. 2005-282693

(51) Int. Cl.
*A61B 1/00* (2006.01)
*A61B 1/04* (2006.01)
(52) U.S. Cl. ......... 600/106; 600/104; 600/114; 600/145
(58) Field of Classification Search .................. 600/106, 600/152, 104, 114, 117, 145, 107; 606/205–209
See application file for complete search history.

(56) References Cited

U.S. PATENT DOCUMENTS

| | | | |
|---|---|---|---|
| 5,817,119 A * | 10/1998 | Klieman et al. | 606/174 |
| 6,554,766 B2 * | 4/2003 | Maeda et al. | 600/132 |
| 6,840,932 B2 * | 1/2005 | Lang | 606/1 |
| 2002/0183592 A1 | 12/2002 | Suzuki et al. | |
| 2003/0040737 A1 | 2/2003 | Merril et al. | |
| 2004/0054258 A1 | 3/2004 | Maeda et al. | |
| 2004/0111081 A1 * | 6/2004 | Whitman et al. | 606/1 |
| 2004/0215060 A1 * | 10/2004 | Ueno et al. | 600/160 |
| 2004/0220449 A1 * | 11/2004 | Zirps et al. | 600/104 |
| 2005/0107669 A1 * | 5/2005 | Couvillon, Jr. | 600/146 |
| 2005/0250989 A1 * | 11/2005 | Suzuki | 600/106 |

FOREIGN PATENT DOCUMENTS

| EP | 1561413 A1 * | 8/2005 |
|---|---|---|
| JP | 57-190541 | 11/1982 |
| JP | 11-244223 | 9/1999 |
| JP | 2000-000207 | 1/2000 |

* cited by examiner

*Primary Examiner* — Thomas J Sweet
*Assistant Examiner* — Ryan Henderson
(74) *Attorney, Agent, or Firm* — Scully, Scott, Murphy & Presser, P.C.

(57) ABSTRACT

An endoscope system comprises an endoscope, medical instrument, operating unit, first and second drive units, and control unit. The endoscope comprises a flexible insertion tube being inserted into an object being examined. The medical instrument is partially inserted into the object through the insertion tube and the operating unit is used for commanding the medical instrument to operate. The first drive unit drives the medical instrument to enable an inserting and pulling-out operation of the medical instrument with the object through the insertion tube. The second drive unit drives the medical instrument to enable the medical instrument to perform a therapeutic operation in the object. The control unit controls drive of the first and second driving devices depending on both an operated state of the operating device and an interference state caused between the medical instrument and the insertion tube when the instrument is actually used.

5 Claims, 20 Drawing Sheets

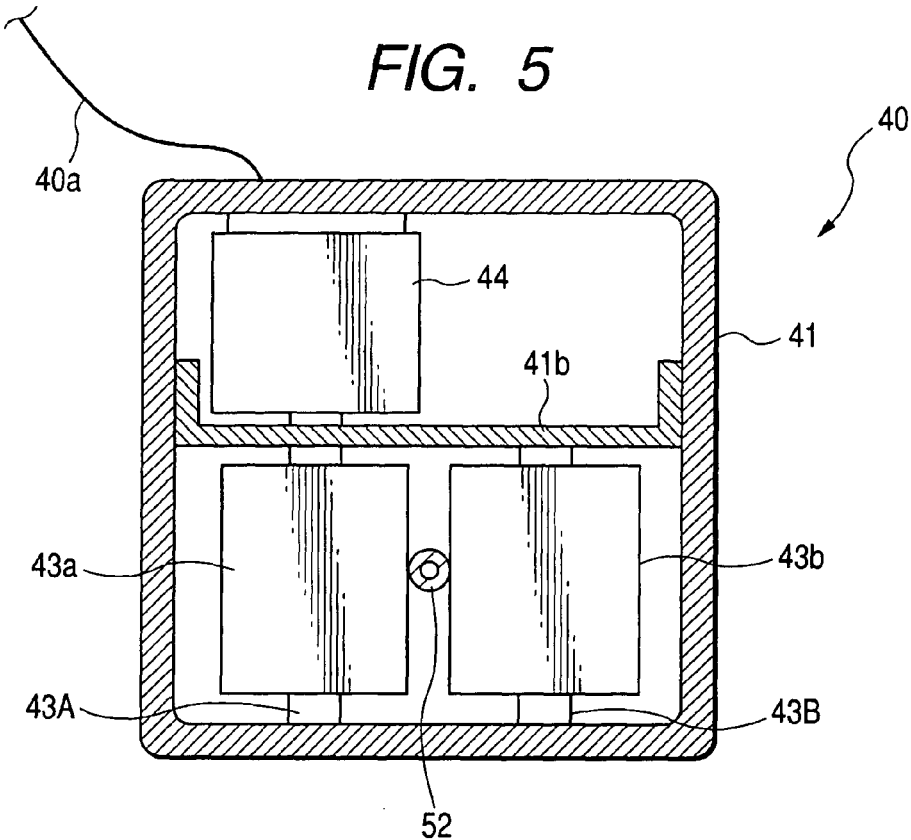
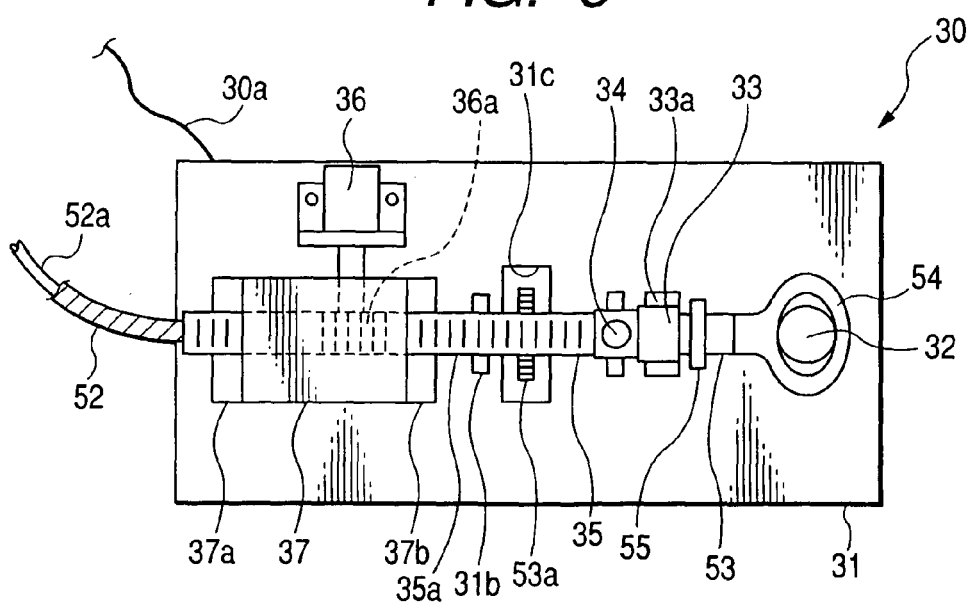

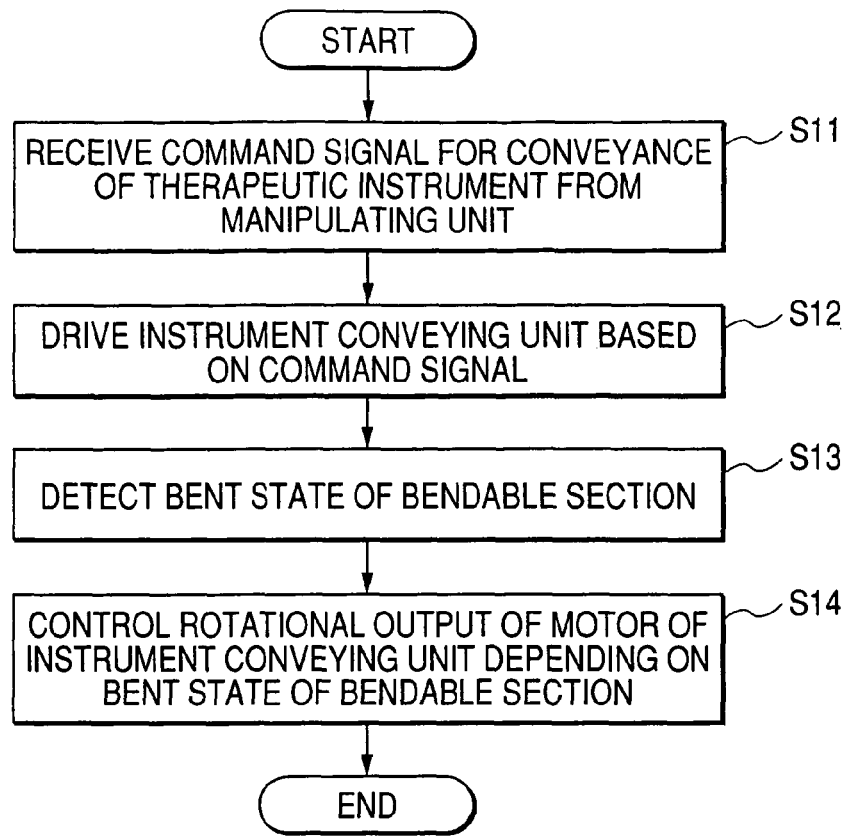
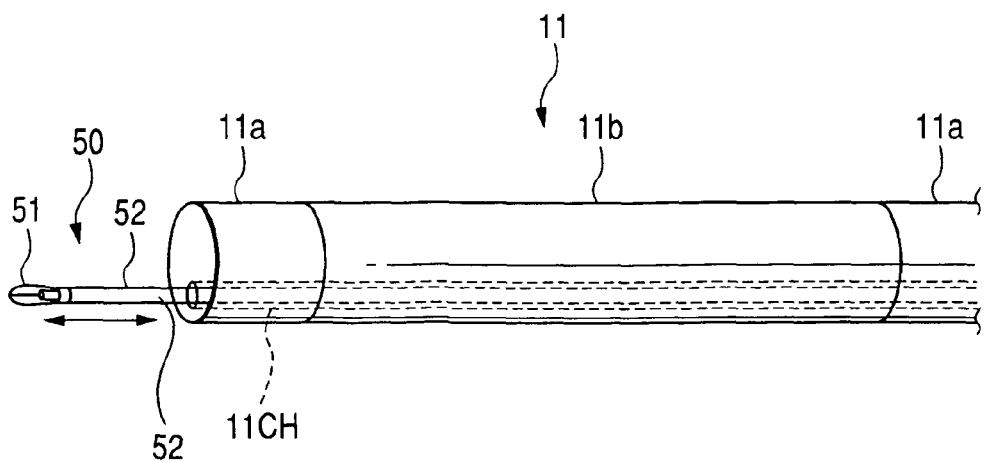

ENDOSCOPE SYSTEM COMPRISING ENDOSCOPE TO WHICH MEDICAL INSTRUMENT IS ATTACHED

CROSS REFERENCE TO RELATED APPLICATION

The present application relates to and Incorporates by reference Japanese Patent application No. 2005-282693 filed on Sep. 28, 2005.

BACKGROUND OF THE INVENTION 1. (The Field of the Invention)

The present invention relates to an endoscope system equipped with an endoscope to which various medical instruments can be attached detachably for use, and in particular, to the endoscope system that improves the operationality of the medical instruments.

2. (Related Art)

Recently, endoscopes have been used widely in the medical field as well as the industrial field. In general, each of these endoscopes is equipped with a thin and elongated insertion tube and an operation unit equipped with various operating members such as knobs and switches for commanding various functions of the endoscope. The insertion tube has a flexibly bendable section located at a distal portion thereof.

In using an industrial endoscope, the insertion tube is Inserted into boilers, gas turbine engines, pipes in chemical plants, bodies of automobile engines, and others, so that portions to be examined can be observed for scratches, cracks, corrosion, and other doubtful damages, and can be tested according to need.

Further, in using a medical endoscope, the insertion tube is Inserted to a body cavity of an object being examined, so that internal organs in the body cavity can be observed and therapeutic instruments Inserted through a therapeutic channel of the endoscope can be used for various types of therapy, if needed.

Especially, in using the conventional medical endoscope, an operator manually inserts a therapeutic instrument into the therapeutic channel with the sheath of the therapeutic instrument held by the operator. In this case, the therapeutic instrument has a length of some 2 m, whereby it takes much time to insert the therapeutic instrument. In addition, the inserting operation must be done with attention. Thus the insertion becomes a troublesome operation for the operator, making operating various therapeutic instruments difficult.

To overcome such difficulties, Japanese Patent Laid-open Publication No. 57-190541 discloses an endoscope that is able to cope with delicate manual inserting operations. That is, the endoscope is provided with a conveying unit for mechanically inserting and pulling a therapeutic instrument into the therapeutic channel of the endoscope. The conveying unit is constructed such that when the therapeutic instrument reaches a position near to the distal portion of the insertion element, the mechanical insertion is released so as to allow the delicate manual inserting operations.

Further, Japanese Patent Laid-open Publication No. 2000-000207 discloses a conveying unit for therapeutic instruments used in combination with an endoscope. In this disclosure, in addition to a configuration that allows therapeutic instruments to be inserted in or pulled out from the therapeutic channel, the conveying unit is equipped with actuating means for actuating a therapeutic member arranged at the tip of each therapeutic instrument and foot switches used to command various inserting and pulling-out operations of the conveying unit.

In operations for a therapeutic instrument, a therapeutic instrument is guided smoothly into the therapeutic channel of an endoscope with the flexibly bendable section bended or is made to smoothly pass the bended bendable section so as to come from the distal portion. In such situations, the larger a curbed angle of the bendable section becomes, the larger the power required for inserting and pulling out the therapeutic instrument. However, the configurations shown by the foregoing two patent publications have a difficulty in a case where the power is set to a value necessary for smooth inserting and pulling-out operations of a therapeutic instrument into and from the bendable section bent at a maximum curve angle thereof. In this case, the bendable section is in a straight (no curved) or in a less curved angle state, the therapeutic instrument is forced to be inserted and pulled out by power larger than an optimally necessary amount, thus making desired inserting and pulling-out operations difficult.

The type of endoscope to be used depends on types of surgeries and different types of endoscopes have therapeutic channels of which diameters are also different from each other. Thus, when the bendable section of an endoscope is bent, a small amount of play between the wall of the therapeutic channel and the sheath of the therapeutic instrument may cause a delay in the response of the inserting and pulling-out operations of the therapeutic instrument.

Additionally, in the case of the configuration shown by the later patent publication, when the bendable section is bent, the similar difficulty to the inserting and pulling-out operations may be caused in a force to open and close such therapeutic instruments as clamping forceps as well as an amount to be open and closed thereof.

SUMMARY OF THE INVENTION

The present invention has been made in consideration of the foregoing various difficulties confronted by the conventional techniques, and has an object to provide an endoscope system capable of raising the operationality of inserting and pulling-out an therapeutic instrument and/or opening/closing the therapeutic member of the therapeutic instrument, regardless of how the medical instrument is interfered from the insertion tube when the medical Instrument is Inserted in and pulled out through the insertion tube.

In order to realize the above object, the present invention provides an endoscope system comprising: an endoscope comprising an elongated flexible insertion tube having a distal end accommodating therein at least an imaging optical system, the insertion tube being inserted into an object being examined; a medical instrument used in combination with the endoscope and partially inserted into the object through the insertion tube; an operating unit used for commanding the medical instrument to operate; a first drive unit configured to drive the medical instrument so as to enable an inserting and pulling-out operation of the medical instrument with the object through the insertion tube; a second drive unit configured to drive the medical instrument so as to enable the medical instrument to perform a therapeutic operation in the object; and a control unit configured to control drive of the first and second driving devices depending on both an operated state of the operating device and an interference state between the medical instrument and the insertion tube, the interference state being caused when the medical instrument is partially inserted in through the insertion tube.

BRIEF DESCRIPTION OF THE DRAWINGS

In the accompanying drawings:

FIG. 5 is a cross sectional view showing the internal configuration of the instrument conveying unit, the view being taken along a lateral direction of the instrument conveying unit;

FIG. 6 is a plan view of an instrument operating unit adopted by the endoscope system;

FIG. 13 is a flowchart exemplifying a fist program executed by the controller for inserting and pulling-out the therapeutic instrument;

FIG. 14 is an illustration explaining how the therapeutic instrument is conveyed through the insertion tube which is almost linearly extended;

DETAILED DESCRIPTION OF THE PREFERRED EMBODIMENTS

With reference to the accompanying drawings, various embodiments of an endoscope system according to the present invention will now be described.

Referring to FIGS. 1 to 32, a first embodiment of the endoscope system will now be described.

Figure 1:
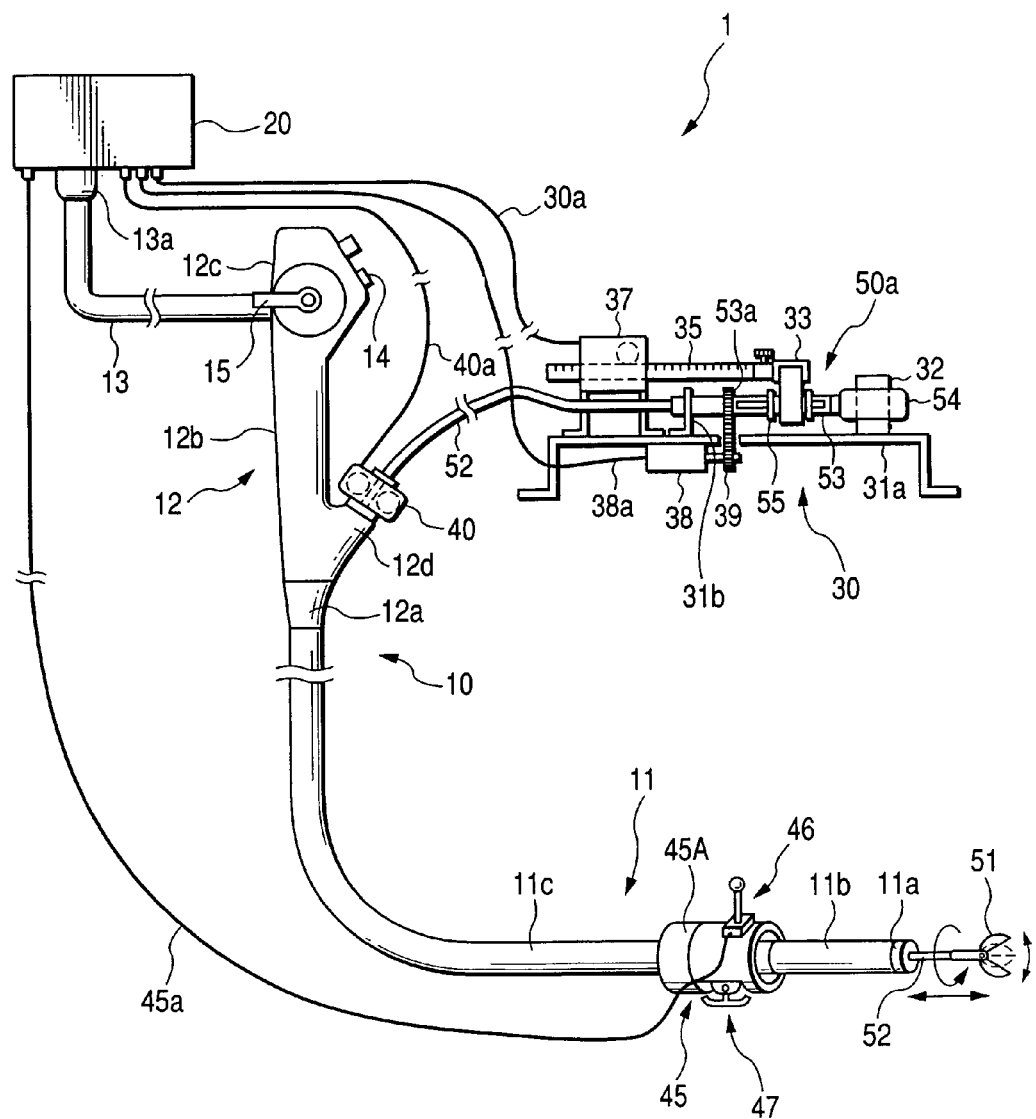
FIG. 1 is a schematic view showing the overall configuration of an endoscope system according to en embodiment of the present invention.

As shown in FIG. 1, an endoscope system 1 is provided which comprises, as its main components, an endoscope 10, a controller 20, an instrument operating unit 30 serving as a second drive unit for medical instruments, an instrument conveying unit 40 serving as a first drive unit for medical instruments, and a manipulating unit 45 serving as an operating unit handled by operators. The controller 20, which functions as a controller, is equipped with an endoscope processor described later, a light source unit (not shown), and a video processor (not shown). In these components, the controller 20, instrument operating unit 30, instrument conveying unit 40, and manipulating unit 45 compose an operation assisting apparatus for assisting operators who handle the present endoscope system. Though not shown, the controller 20 is connected to display means, such as monitors, for displaying images acquired by the endoscope.

Figure 2:
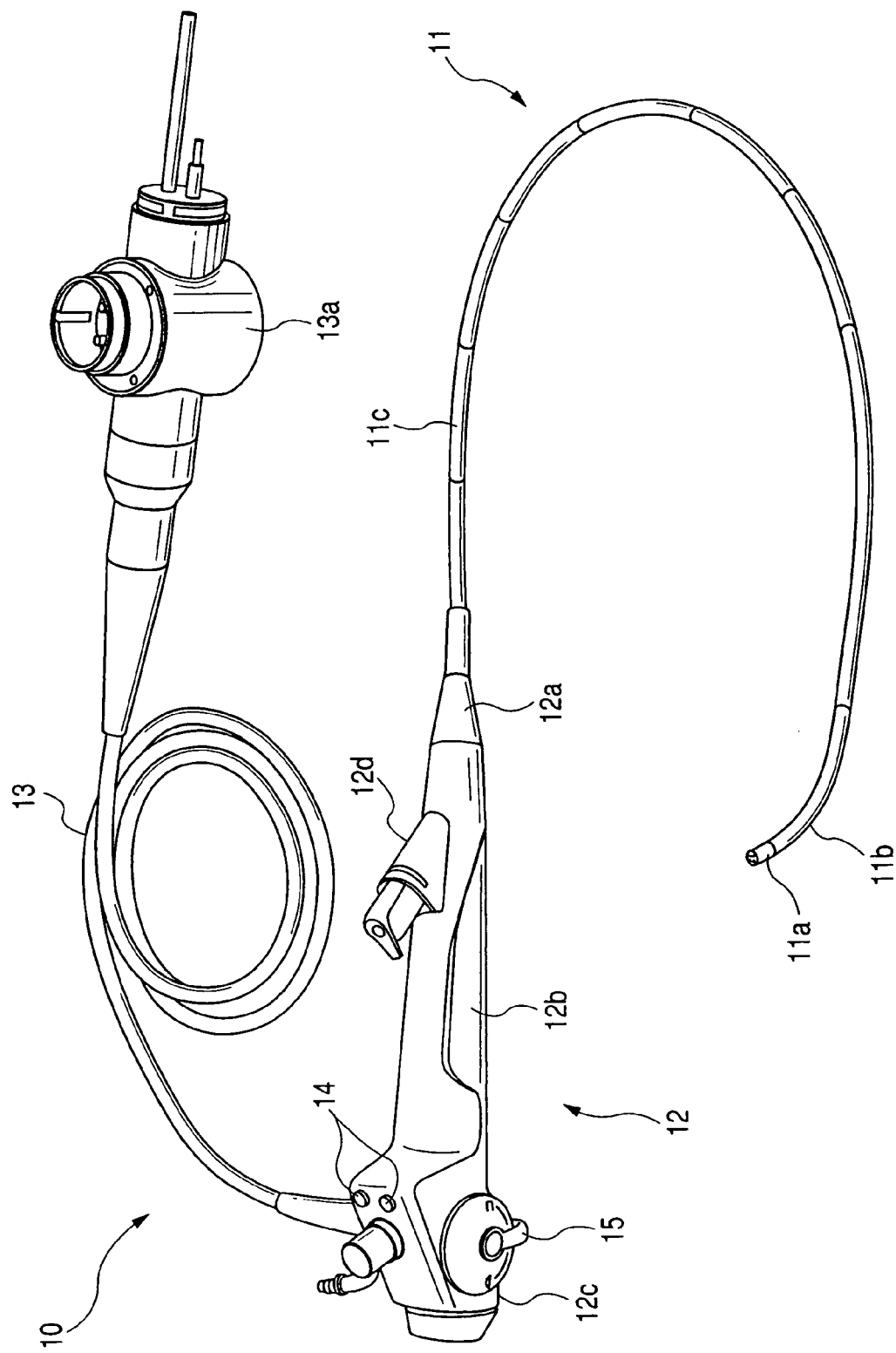
FIG. 2 is a schematic view showing the configuration of an endoscope adopted by the endoscope system.

The endoscope 10 is detailed in FIG. 2, in which the endoscope 10 is provided with a thin and elongated insertion tube 11, an operating base holder 12 rigidly connected to a base end of the insertion tube 11, and a universal code 13 connecting the operating base holder 12 and the controller 20.

The insertion tube 11 is a soft tubular member composed of a distal section 11a, a Flexibly bendable section 11b, and a flexible tubular section 11c, which are positioned and mutually rigidly connected in this order from the distal end thereof, but are flexible and bendable as a whole. Further, the operating base holder 12 is composed of an anti-bending base portion 12a to which a base end of the flexible tubular section 11c is rigidly connected, a grasping portion 12b provided with an instrument inserting portion 12d, and a main operation portion 12c connected to the base portion 12a via the grasping portion 12b. All the portions 12a to 12d are rigidly combined to form a single body that is the operating base holder 12. Of these, the main operation portion 12c is provided with a bending lever 15 as well as plural switches used for commanding air supply, water supply, suction, and various optical operations for imaging means and illuminating means disposed in the distal section 11a. The bending lever 15 is used to command a bend at the bendable section 11b.

In this endoscope 10, a therapeutic channel 11CH (thin and elongated tubular bore; refer to FIG. 14), through which various therapeutic instruments are inserted and pulled out (that is, conveyed), is formed to range from the instrument inserting portion 12d to the distal section 11a through the insertion tube 11, which will be detailed later. The universal code 13 has a base end at which a connector 13a is disposed for connection with the controller 20.

Figure 31:
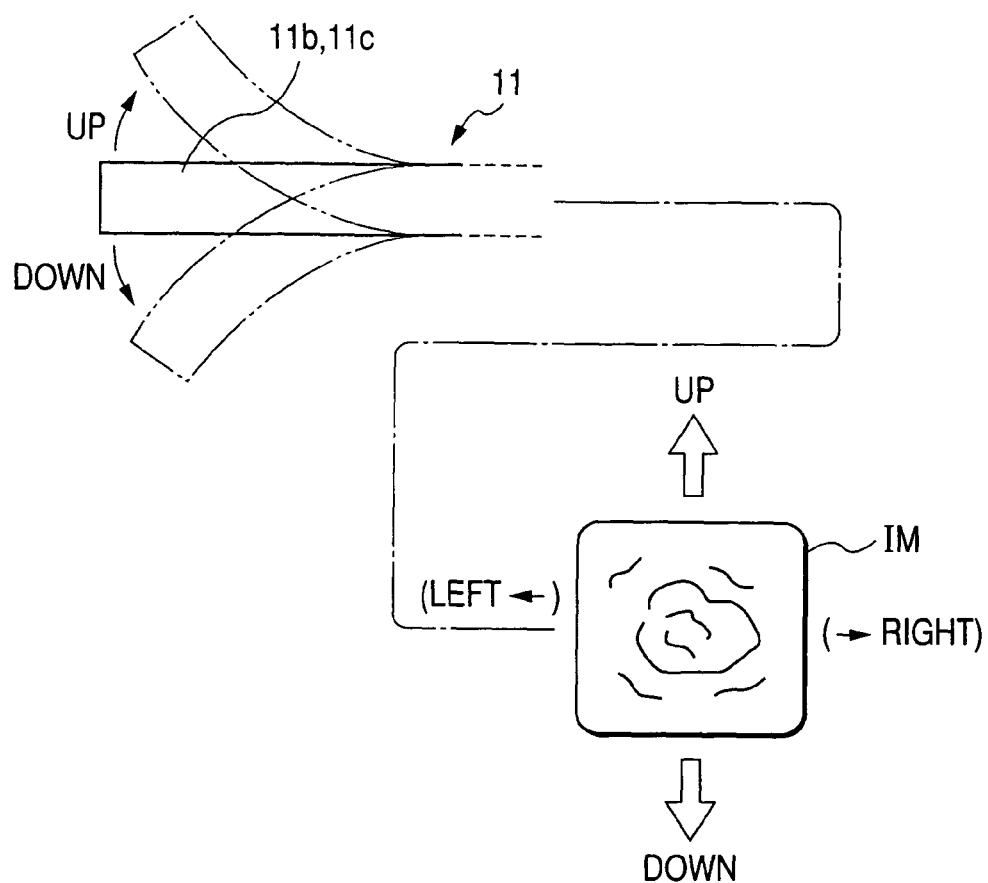
FIG. 31 is an illustration explaining the definition of the upward and outward directions.

In the endoscope 10 employed in the present embodiment, the bendable section 11b is electrically driven to be bent in two ways consisting of the upward and downward directions. In the present embodiment, the upward and downward directions are defined as follows. As illustrated in FIG. 31, during display of endoscope images IM on the screen, when the bendable section 11b is bent to allow the images to move upward, the motion of the bendable section 11b is defined as being bent in the upward direction (UP), whilst when the bendable section 11b is bent to allow the images to move downward, the motion of the bendable section 11b is defined as being bent in the downward direction (DOWN). In another type of endoscope that allows 4-way motions of the bendable section 11b, this theory is also true of the rightward and leftward directions (RIGHT and LEFT).

The bending lever 15 on the operation unit 15 is used for such bending operations and the endoscope 10 is constructed to respond to such operations so that the bendable section 11b moves upward or downward. However, this bending system is not a decisive list. For example, the endoscope 10 can be formed into another type that allows the bendable section 11b to be bent in four ways consisting of the upward, downward, rightward, and leftward directions (or the circumferential direction around a longitudinal axis of the bendable section 11b depending on the operations for the four ways).

The instrument operating unit 30 is electrically connected to the controller 20 via an electric cable 30a and accepts a handle 53 of the therapeutic instrument 50 which is a medical instrument such as a clamping forceps. In the same way, the instrument conveying unit 40 is electrically connected to the controller 20 via another electric cable 40a and secured at the instrument inserting portion 12d of the endoscope 10.

The therapeutic instrument 50 comprises a therapeutic member 51 located at the distal end thereof, an operating wire 52a of which one end is coupled with the therapeutic member 51 for operations, a tubular sheath 52 containing therein the operating wire 52a such that the wire 52a passes through the sheath 52 and is rotatable about an axis of the wire 52a, and the foregoing handle 53 coupled with the other end of the operating wire 52a. For use of the therapeutic instrument 50, this instrument 50 is subjected to its inserting and pulling-out operations into a body cavity of an object being examined. Such inserting and pulling-out operations are carried out by making the sheath 52 insert and pull out, as will be described. Thus inserting and pulling out the sheath 52 means that the operating wire 52a contained in the sheath 52 and the therapeutic member 51 located at the distal end are inserted and pulled out together with the sheath 52.

Through this instrument conveying unit 40, the sheath 52 (together with the operating wire 52a) of the therapeutic instrument 50 is driven to be guided into the therapeutic channel 11CH. The manipulating unit 45 is also electrically connected to the controller 20 via a signal cable 45a and loaded on the outer surface of the insertion tube 11.

In the present embodiment, the therapeutic instrument 50 is exemplified as the clamping forceps, as stated above, so that the therapeutic member 51 is composed by the grip portion of the clamping forceps. The sheath 52 of this therapeutic instrument 50 is inserted into the therapeutic channel 11CH in such a manner that the sheath 52 is made to freely advance and go back, thus making it possible that the therapeutic member 51 appears from and disappear into the opening of the therapeutic channel 11CH in the front of the distal section 11a of the insertion tube 11.

Figure 3:
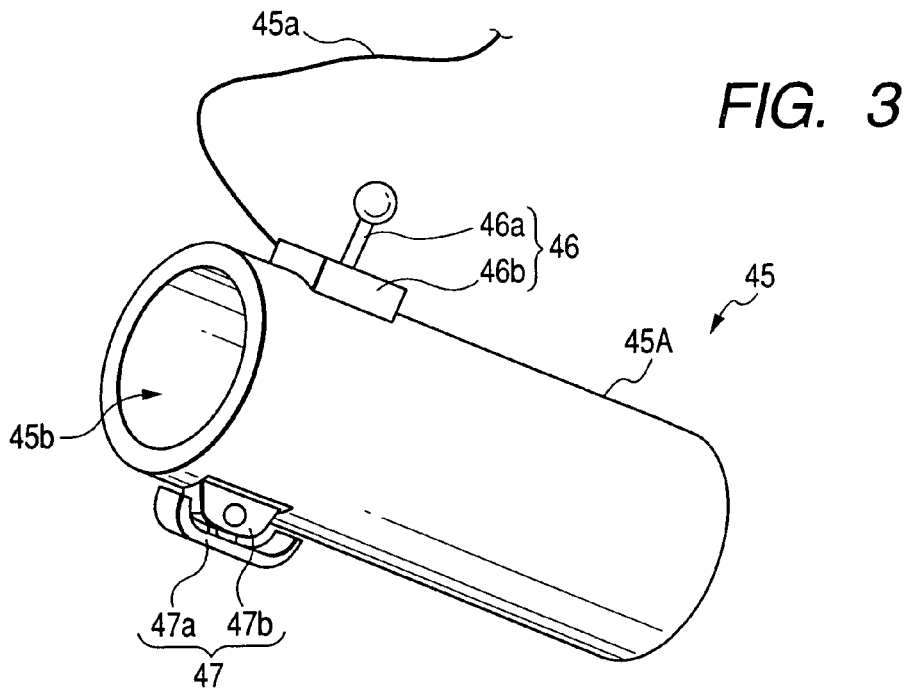
FIG. 3 is a schematic view showing the configuration of a manipulating unit adopted by the endoscope system.

With reference to FIG. 3, the manipulating unit 45 will now be detailed. As shown, the manipulating unit 45 is provided with a substantially tubular member 45A in which an insertion through-hole 45b is formed. On a distal-side outer surface of this tubular member 45A, there is formed and attached an operation commanding portion 46 consisting of an operation lever 46a and a lever supporter 46b. Further, on another distal-side outer surface of this tubular member 45A, a rotation commanding portion 47 is provided so as to be positioned oppositely to the operation commanding portion 46.

The foregoing signal cable 45a extends from the lever supporter 46b. The rotation commanding portion 47 is electrically connected with the signal cable 45a connected with the controller 20 and also extended from the operation commanding portion 46.

The rotation commanding portion 47 is composed of a rotation lever 47a rotatably operated about an axis perpendicular to an axial direction of the manipulating unit 45 and a lever supporter 47b rotatably supporting the rotation lever 47a.

In this description, the distal-end side of the tubular member 45A indicates a head-end side in a direction along which the insertion tube 11 with the manipulating unit 45 loaded thereon is inserted into a body cavity of an object being examined. Accordingly, as shown in FIG. 1, the insertion tube 11 is inserted into the insertion through-hole 45b of the tubular member 45A from the opening at the base-side end thereof, resulting in that the manipulating unit 45 is loaded on the outer surface of the insertion tube 11. The inner diameter of the insertion through-hole 45b is set to be larger than the outer diameter of the insertion tube 11, thereby the manipulating unit 45 loaded on the insertion tube 11 being slidable along a longitudinal direction of the insertion tube 11.

By the way, the signal transmission from the manipulating unit 45 to the controller 20 is not necessarily limited to use of the signal cable 45a, but may rely on a wireless system. That is, the manipulating unit 45 may be provided with a wireless transmitter to transmit command signals, generated from the commanding portions 46 and 47 in response to operator's operations, to the controller 20. In this case, the controller 20 is of course provided with a wireless receiver to receive such command signals from the manipulating unit 45.

Figure 4:
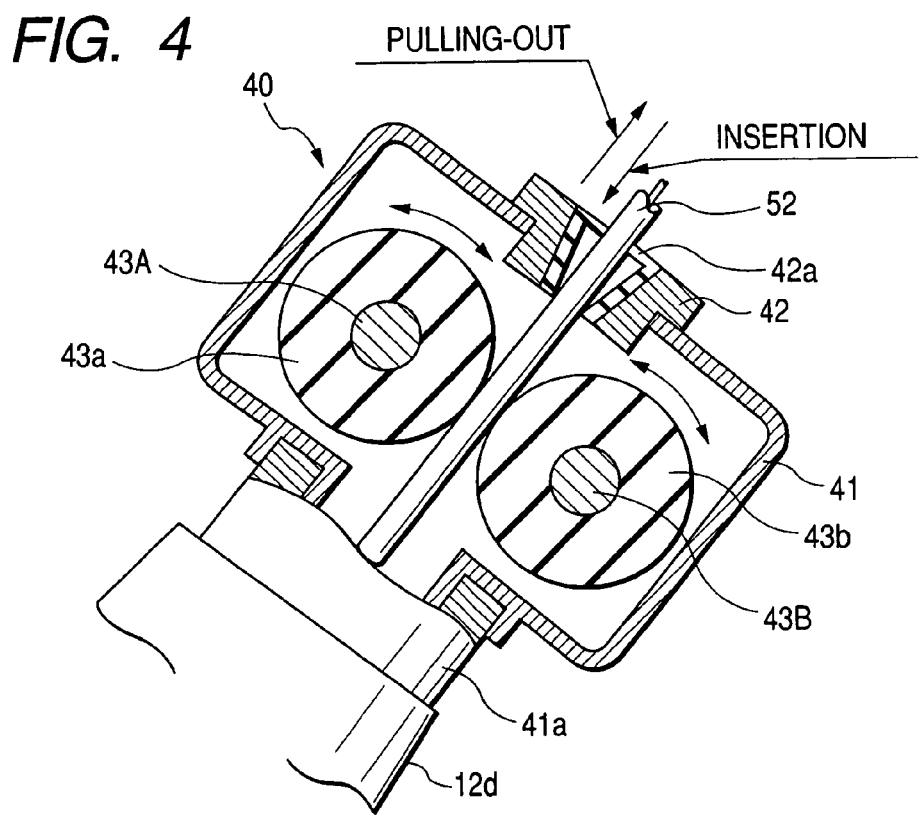
FIG. 4 is a cross sectional view showing the internal configuration of an instrument conveying unit adopted by the endoscope system, the view being taken along a longitudinal direction of the instrument conveying unit.

Referring to FIGS. 4 and 5, the instrument conveying unit 40 will now be detailed.

As shown in FIG. 4, the instrument conveying unit 40 is provided with a substantially box-shaped member 41 and two rollers 43a and 43b rotatably arranged within the box-shaped member 41. In one of the walls forming the box-shaped member 41, formed is an insertion hole portion 42 through which the sheath 52 of the therapeutic instrument 50 is inserted, while in the opposite wall to the wall with the insertion hole portion 42 formed; formed is a scope fixing member 41a. This scope fixing member 41a guides the sheath 52 into the therapeutic channel 11CH of the endoscope 10 and is used as a connection to the instrument inserting portion 12d of the endoscope 10.

The insertion hole portion 42 is filled with a forceps plug 42a made from elastic material, in which the forceps plug 42a still has an insertion hole through which the sheath 52 is slidably inserted and pulled out. Meanwhile the scope fixing member 41a is linked with the opening of the therapeutic channel 11CH at the instrument inserting portion 12d in an airtight manner. As a result, when the sheath 52 is inserted or pulled out in a case where the body cavity is expanded by air supply or water supply via the endoscope 10 in order to facilitate an easy observation therein, the forceps plug 42a and scope fixing member 41a keep the air tightness of the therapeutic channel 11CH so as to prevent a drop in the pressure within the body cavity.

The two rollers 43a and 43b in the box-shaped member 41 are made from, for example, elastic material and rotatable by rotation shafts 43A and 43B, respectively. Both rollers 43a and 43b press, by their rotations, the outer surface of the sheath 52, placed in a gap formed between the rollers 43a and 43b, so as to allow the sheath 50 to go forward and go back through the therapeutic channel 11CH.

Of both rollers, one roller 43a is a driving roller and its rotation shaft 43A is driven by an electric motor 44 placed in the box-shaped member 41 (refer to FIG. 5). Meanwhile the other roller 43b is a driven roller of which rotation helps the sheath 52 move smoothly which go forward and backward in response to the rotation of the driving roller 43a.

The rollers 43a and 43b are rotatably supported from the side walls and a supporting plate 41b in the box-shaped member 41 such that the rollers 43a and 43b are spaced apart from each other to form the respective roller surfaces a gap of predetermined length therebetween and the respective rotation shafts 43A and 43B are in parallel to each other.

Figure 7:
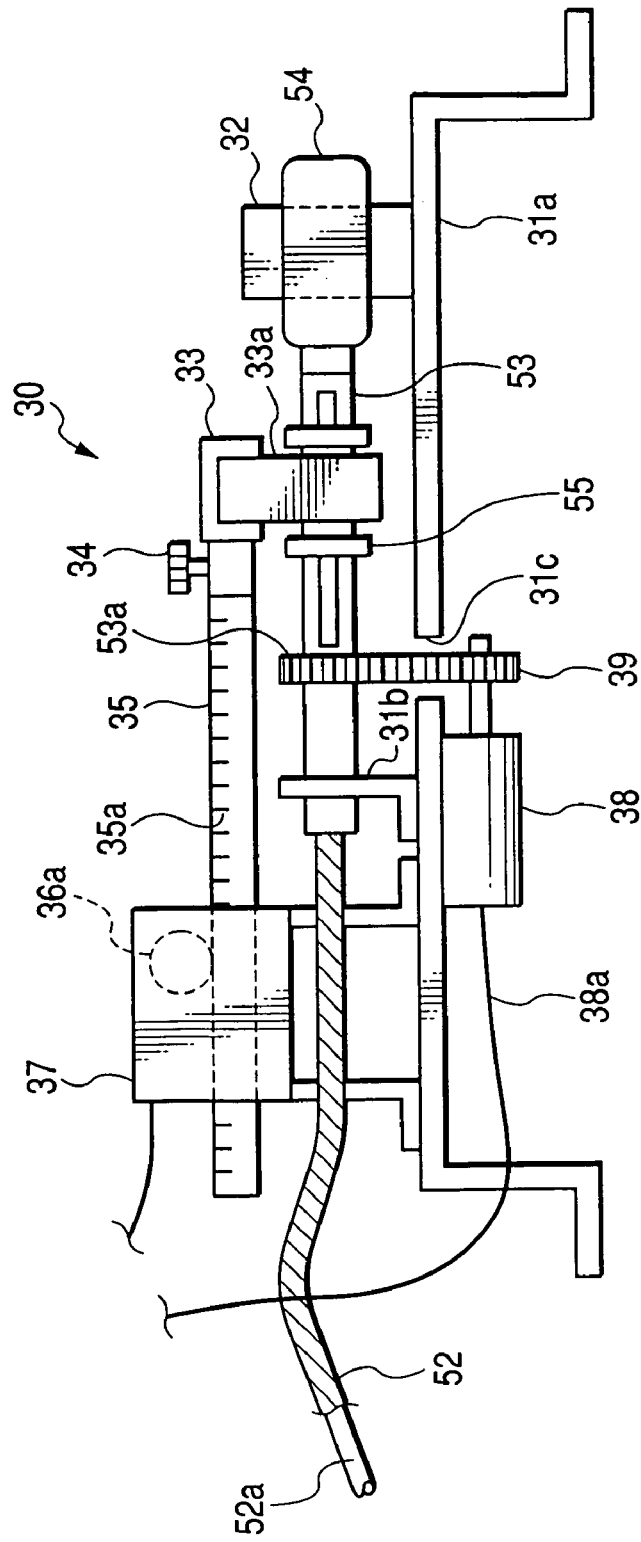
FIG. 7 is a side view of the instrument operating unit.

Referring to FIGS. 6 and 7, the instrument operating unit 30 will now be detailed. As shown, the instrument operating unit 30 is provided with a plate-like base 31a, a ring holding member 32 protruded from a surface of the base 31a, a slider holding member 33 pinching a slider 55 of the therapeutic instrument 50, and other some components including a rack 35, a motor 36, a holding box 37, and an electric motor 38. Of these, the rack 35 is linked with the slider holding member 33. The motor 36 has a rotation shaft on which a pinion gear 36a is secured so as to engage with a liner gear portion 35a of the rack 35. The holding box 37 is secured on the base 31a by securing members 37a and 37b and accommodates therein the pinion gear 36a, and holds the rack 35 to allow its linear motions for free inserting and pulling-back operations. The motor 38 is placed to revolve the sheath 52 and the therapeutic member 51 on the axial direction of the sheath 52 from the distal end of the handle 53 of the therapeutic instrument 50.

The ring holding member 32 is arranged so as to be inserted into a finger-engaging ring 54 of the therapeutic instrument 50, so that the handle 53 is held at the instrument operating unit 30. The ring holding member 32 is shaped into a column having an outer diameter substantially equal to an inner diameter set to the finger-engaging ring 54, thus securely holding the handle 53, that is, the therapeutic instrument 50. Incidentally the outer diameter of the ring holding member 32 may be formed to have a dimension slightly smaller than the inner diameter of the finger-engaging ring 54, if the ring holding member 32 is used with an elastic tube member mounted on the outer surface of the member 32. Employing this manner allows the handle 30 to be securely held by the instrument operating unit 30.

As shown in FIGS. 6 and 7, the slider holding member 33 is formed to have two holding plates 33a extending in an up-and-down direction perpendicular to the base 31a, in which the holding members 33a hold the slider 55 of the therapeutic instrument 50 by pinching the slider 55 by the sides. Specifically, the slider 55 is formed into a drum-like shape having a flange on each of both axial end sides thereof, so that the two holding members 33a are placed to pinch its body portion existing between the flanges. The slider holding member 33 is linked with one end of the rack 35 by a setscrew 34, as described before.

The pinion gear 36, which can be rotated together with the rotation of the motor 30, is engaged with the linear gear portion 35a. Thus the rotation of the pinion gear 36 will cause the rack 35 to selectively move forward and backward in the axial (longitudinal) direction of the handle 53. This movement becomes relative motions to the holding box 37. Thus the slider holding member 33 allows the slider 55 to move along the handle 53 for inserting and pulling-out operations of the therapeutic instrument 50.

By the way, the therapeutic instrument 50 has an operating wire 52a that passes through the bore of the sheath 52, and a distal end of the operating wire 52a is linked to the therapeutic member 51 and the other base end is linked to the slider 55. In response to the forward and backward motions of the sliders 55 in the axial direction of the handle 53, the operating wire 52a is pulled or relaxed so that these pulling and relaxation motions are converted to given operations of the therapeutic operations. In the present embodiment, the therapeutic member 50 is a clamping forceps, so that the given motions are open and close operations of a gator-grip-shaped gripping portion thereof.

The motor 38 has a rotary shaft whose end has a spur gear 39 for transmitting the rotation from the rotary shaft and is connected to the controller 20 via the signal cable 38a. As shown in FIG. 7, this motor 38 is secured on the back of the base 31a, which is formed to have a depressed back space.

Further, the base 31a has a given-size through-hole 31c formed therethrough and located to coincide with the position of the gear 39 of the motor 38 arranged on the back side. On the front surface of the base 31a, there is arranged a holding member 31b to rotatably hold the distal end portion of the handle 31b.

At a predetermined intermediate part of the handle 53, there is provided a driven gear 53a engaged with the gear 39 that appears through the through-hole 31c of the base 31a.

Figure 8:
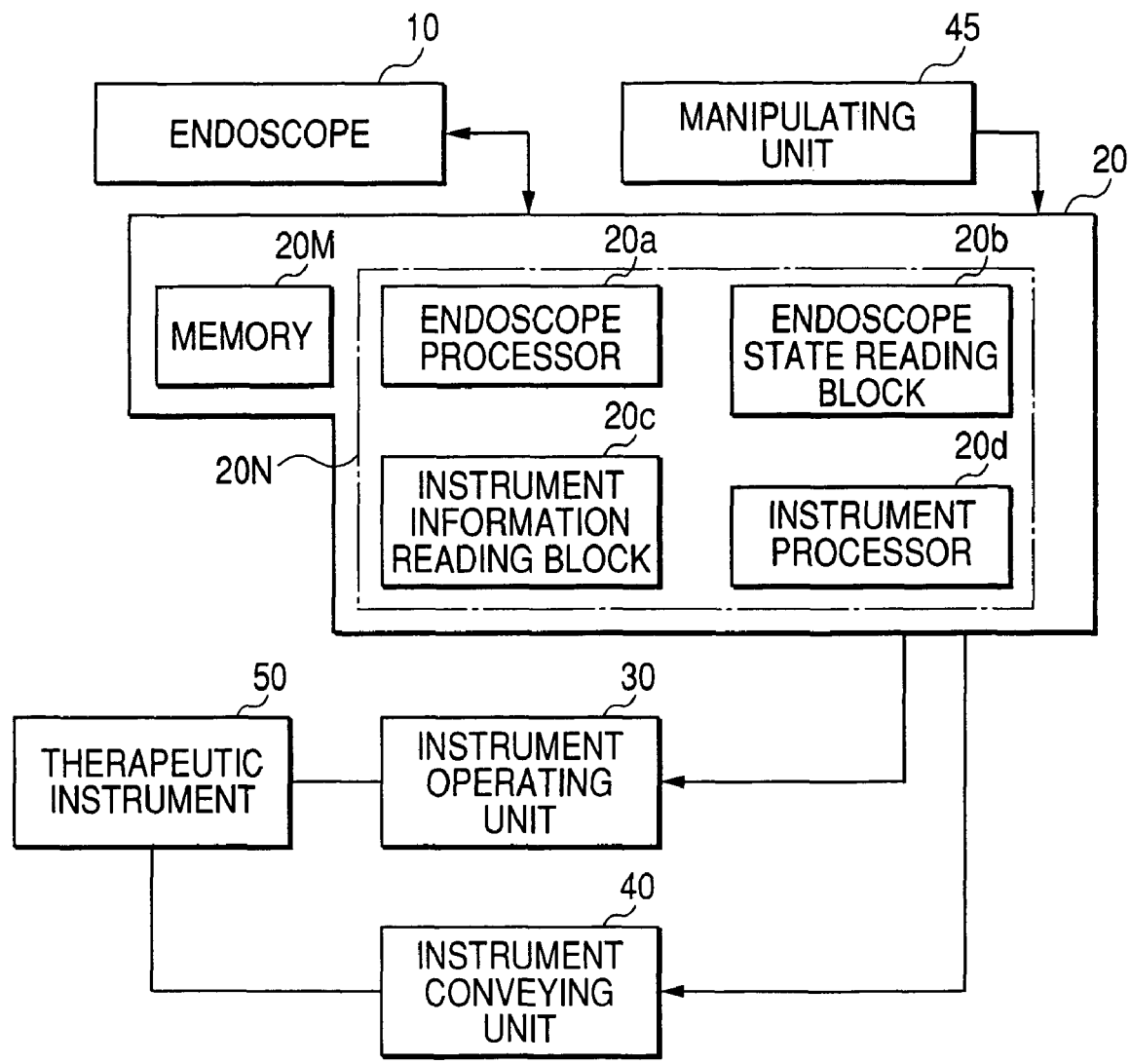
FIG. 8 is a block diagram outlining an electrical configuration of the endoscope system according to the embodiment.

Referring to FIG. 8, the controller 20 will now be described. As shown, the controller 20 is provided with a CPU (central processing unit) 20N, a memory 20M, and other necessary components, which are formed as a computer system. Hence programs previously stored in the memory 20M enable the CPU 20N to work, whereby control can be performed on the programs in a desired manner. The operations of the CPU 20N functionally realizes an endoscope processor 20a as well as an endoscope state reading block 20b, an instrument information reading block 20c, and an instrument processor 20d.

Though not detailed, the endoscope processor 20a is in charge of performing not only processing inherently necessary for the endoscope 20, which relates to processing for air supply, water supply, illumination and imaging but also processing necessary for the therapeutic instrument 50. To be specific, the endoscope processor 20a reads, via the connector 13a of the universal code 13 connected to the controller 20, information indicative of the type of scope which expresses a scope ID of the endoscope 10 and information indicative of the bent state of the bendable section 11b from an electric output required for bending the bendable section 11b. The information indicative of the type of scope includes pieces of information about materials of the endoscope 10, the length and outer diameter of the insertion tub 11, the length and diameter of the therapeutic channel 11CH, and a layout of various optical systems and an opening of the therapeutic channel 11CH positioned in the front of the distal section 11a.

The endoscope state reading block 20b operates to read a bent state of the bendable section 11b from signals including a signal commanding the bendable section 11b to bend in response to operations at the bending lever 15 and signals coming from a potentiometer and an encoder arranged in the endoscope 10. Further, the instrument information reading block 20c reads, from ID information about the therapeutic instrument 50 (a therapeutic Instrument ID), information indicative of instrument materials, the length of outer diameter of sheath 52, and the type of the therapeutic member 51.

Furthermore, the instrument processor 20d receives information read by the endoscope processor 20a and both the reading blocs 20b and 20c. And using the received information and the various operation signals coming from the manipulating unit 45, the instrument processor 20d produces drive signals and provides them to the instrument operating and conveying units 30 and 40, respectively. This drive allows the therapeutic member 51 to open and close and the sheath 52 (i.e., the therapeutic instrument 50) to be inserted and pulled out and rotated.

Figure 9:
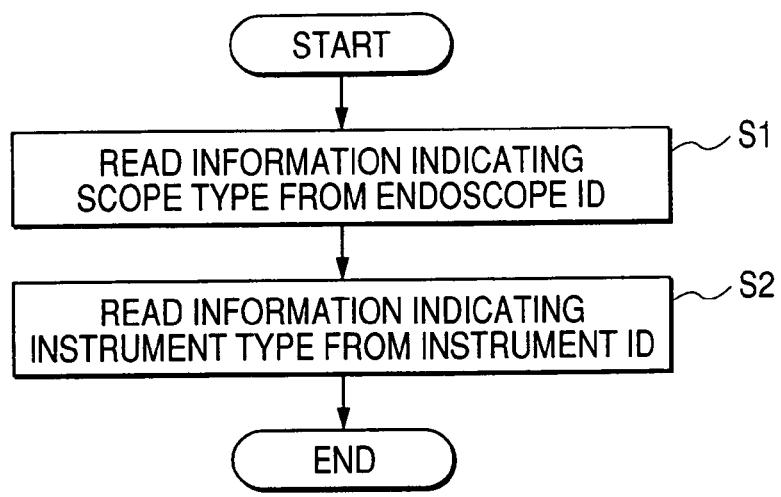
FIG. 9 is a flowchart explaining processing conducted by a controller of the endoscope system when the endoscope system is set.

Thus, when the therapeutic instrument 50 is set to the endoscope system 1 as described, the endoscope processor 20d is activated according to the Steps shown in the flowchart in FIG. 9. First the therapeutic processor 20d reads out, from the endoscope ID, information indicating the scope type of the endoscope 10 (Step S1), and reads out, from the therapeutic instrument ID, the instrument type of the therapeutic instrument 50 (Step S2). In the present embodiment, the information indicating the endoscope ID is obtained from an IC chip embedded in for example the handle 53 via the instrument operating unit 30. Of course, this information may be manually inputted. Meanwhile the endoscope ID, can be inputted by operator's manual operations at a not-shown operation device of the endoscope system 1. By the way, the information indicating the types of the endoscope 10 and therapeutic instrument 50 may be inputted to the controller 20 (i.e., the endoscope processor 20d) via a bar code system.

The operations and advantages of the endoscope 1 will now be described. The whole description will now be given to those operations and advantages, which will be followed by describing examples of control of inserting/pulling-out operations and driving operations of the therapeutic instrument 50.

Figure 10:
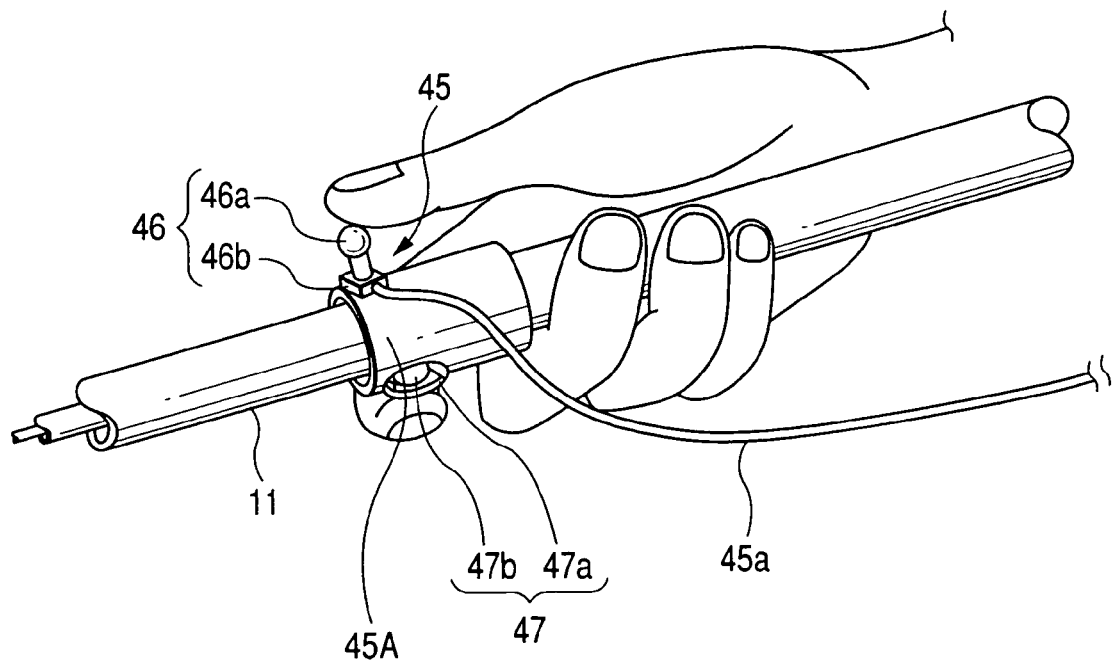
FIG. 10 shows a state where the manipulating unit is loaded on an insertion tube of the endoscope and gripped by a hand of a user.

As shown in FIG. 10, an operator (e.g., doctor) loads the manipulating unit 45 on the insertion tube 11 of the endoscope 10 so that the tube 11 passes through the unit 45, and inserts the insertion tube 11 into a body cavity of an object being examined. The operator examines the body cavity with monitoring acquired endoscope images, during which time when a lesion is found in the cavity, the operator is able to treat the lesion by performing various therapeutic operations such as ablation. In the present embodiment, use of the clamping forceps is described.

In this case, like the foregoing, the manipulating unit 45 is first loaded on the insertion tube 11, and then the handle 53 of the therapeutic instrument 50 is fixed at the instrument operating unit 30. Concretely, the operator the slider holding member 33 with the rack 35 removed is loaded on the slider 55 so as to put the ring holding member 32 in the finger-engaging ring 54 of the handle 53.

Then the operator puts the distal end of the therapeutic instrument 50 through the holding member 31b to load the distal end of the handle 53 onto the holding member 31b in a rotatable member, and then inserts the finger-engaging ring 54 of the handle 53 into the ring holding member 32. The gear 53a of the handle 53 and the gear 39 exposed through the through-hole 31c of the base 31a are made to engage with each other. As shown in FIG. 7, the operator uses the screwset 34 to connect the slider holding member 33 and the rack 35 with each other.

The operator then proceeds to loading the instrument conveying unit 40 to the instrument inserting portion 12d. Through the unit 40, the sheath 52 is inserted into the therapeutic channel 11CH of the endoscope 10 so that its therapeutic member 51 advances therein at the head. In the work, the operator continues the insertion until the therapeutic member 51 passes the two rollers 43a and 43b in the instrument conveying unit 40 to allow the sheath 52 to begin being pressed between the two rollers 43a and 43b. Alternatively, the operator may manually carry out an initial insertion, in which the sheath 52 is continued to be inserted into the therapeutic channel 11CH until the therapeutic member 51 reaches the distal end of the insertion tube 11 (i.e., the therapeutic channel).

With observing endoscopic images, the operator then inserts the insertion tube 11 into a body cavity of the object so that the distal section 11a at the head in the cavity. And when a lesion is found in the cavity, the operator should hold the distal section 11a in the body cavity so that the view range of the endoscope 10 surely captures the lesion. For keeping such a viewing location, the operator is to not only grip the insertion tube 11 by one hand (for example, the left and) but also concurrently hold (grip) the manipulating unit 45 by the other hand (for example, the right hand). In this grip, as shown in FIG. 10, the operator uses her or his fingers for gripping, where the first finger wraps the approximately cylindrical outer surface of the manipulating unit 45 so that the first finger touches the rotation lever 47a, the thumb touches the operation lever 46a, and the remaining middle to little fingers grip the insertion tube 11.

Figure 11A:
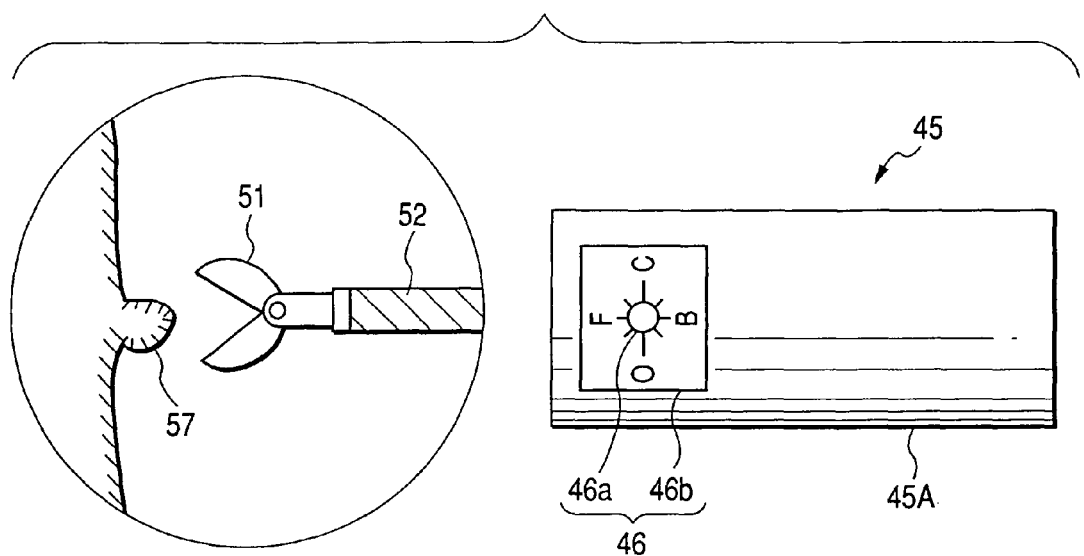
FIGS. 11A and 11B are illustrations each exemplifying inserting and open/close operations of a therapeutic instrument which are responsive to commands from the manipulating unit.
Figure 11B:
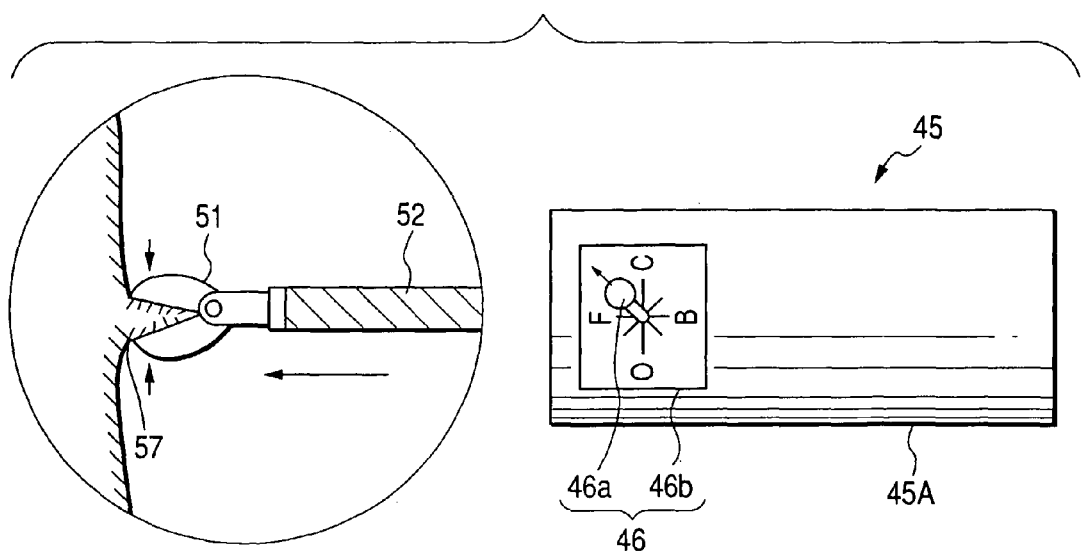

The operator performs therapy at a lesion such as a polyp in the body cavity using endoscopic images being acquired in real time. During this therapy, the operator uses the manipulating unit 45, held by the one hand, together with the insertion tube 11, to manipulate the operation lever 46a. As shown in FIGS. 11A and 11B, tilting the operation lever 46a in the predetermined directions makes it possible that the therapeutic member 51 is opened and closed and the sheath 52 is conveyed along its axial direction, that is, operated to be inserted and pulled out.

In the present embodiment, there are printed markings on the upper surface of the lever supporter 46b. The markings include references "F", "B", "O" and "C". When the operator operates the operation lever 46a so that it is tilted toward the reference "F" (a direction advancing to the distal end of the lever supporter 46; i.e., the inserting direction along the axis of the insertion tube 11), the sheath 52 can be conveyed to advance (i.e. inserted) toward the distal end of the insertion tube 11. On the contrary, when the operator operates the operation lever 46a so that it is tilted toward the reference "B" (a direction going back to the base end of the lever supporter 46; i.e., the going-back direction along the axis of the insertion tube 11), the sheath 52 can be conveyed to go back (i.e., pulled out) toward the base end of the insertion tube 11.

Similarly, in response to an operator's manual operation at the operation lever 46a toward the left perpendicular to the axial direction of the lever supporter 46 (i.e., toward the reference "O" in FIG. 11A), the therapeutic member 52 can be opened. In response to the opposite operation toward the rightward (i.e., toward the reference "C" in FIG. 11A), the therapeutic member 52 can be closed.

That is, making the operation lever 46a tilt in the forward and backward directions (in the directions shown by the references "F" and "B"), the resultant command signals are fed to the instrument processor 20d via the signal cable 45a. Responding to the command signals, the instrument processor 20d powers the instrument conveying unit 40 via the electric cable 40a so as to rotate the motor (refer to FIG. 5) of the unit 40 in the predetermined direction. The rotation of the motor 44 allows the driven roller 43a of the unit 40 to rotate in the predetermined direction, with the result that the sheath 52 held, in a pressed manner, between the two rollers 43a and 43b begins to move forward or backward (i.e., inserted or pulled out) in the therapeutic channel 11CH of the endoscope 10.

Accordingly, the operator is able to move the therapeutic member 51 to appear or disappear from or into the front of the distal section 11a of the insertion tube 11 by operating the operation lever 46a of the manipulating unit 45 to be tiled back and forth.

Furthermore, an operator's rightward or leftward tilting operation of the operation lever 46a (i.e., toward the direction shown by the reference "O" or "C") produces a command signal fed to the instrument processor 20d via the signal cable 45a. Responsively to this command signal, the instrument processor 20d powers the instrument operating unit 30 via the electric cable 30a so as to allow the motor 36 of the unit 30 to rotate in the predetermined direction.

In association with the rotation of the pinion gear 36a, driven by the motor 36, the liner gear portion 35a is driven depending on the rotational directions of the pinion gear 36a. Hence the rack 35 is forcibly moved linearly back and forth relatively to the holding box 37. Accordingly the slider holding member 33 coupled with the rack 35 is allowed to move the slider 55, which has been held so far by the member 33, in the backward or forward direction along the axis of the handle 53. This movement of the slider 55 gives traction or relaxation to the operating wire 52a of the therapeutic instrument 50.

Accordingly, the operator can operate the operation lever 46a to be tilted rightward or leftward in a selective fashion, so that the therapeutic member 51 can be opened and closed.

In addition, in the present embodiment, the operator is allowed to make the operation lever 46a to tilt toward each of four middle areas sectioned by the back and forth directions (the references "F" and "B") and the right and left directions (the references "O" and "C"). By operating the lever 46a toward any of those four middle areas, the operator is allowed to perform various patterned operations in which the appearance and disappearance operations of the therapeutic member 51 from the distal section 11a of the insertion tube 11 and the open and close operations of the therapeutic member 51 are simultaneously combined with each other. One pattern is exemplified in FIG. 11B, where the operation lever 46a is tilted toward a middle area between the references "F" and "C". Responsively to this operation, the therapeutic member 51 is made to not only extend outward from the end of the insertion tube 52 toward a region 57 being treated but also the therapeutic member 51 is closed to grip the lesion.

Additionally, depending on how deep the operation lever 46a is tilted, the inserting and pulling-out operations of the sheath 52 (i.e., the therapeutic instrument 50) and the open/close operations of the therapeutic instrument 50 can be controlled in terms of their operation speeds. In the present embodiment, the setting is made such that the deeper the tilt angel of the operation lever 46a (an angle tilted from an angle given at its initial position), the larger the operation speeds.

Figure 12:
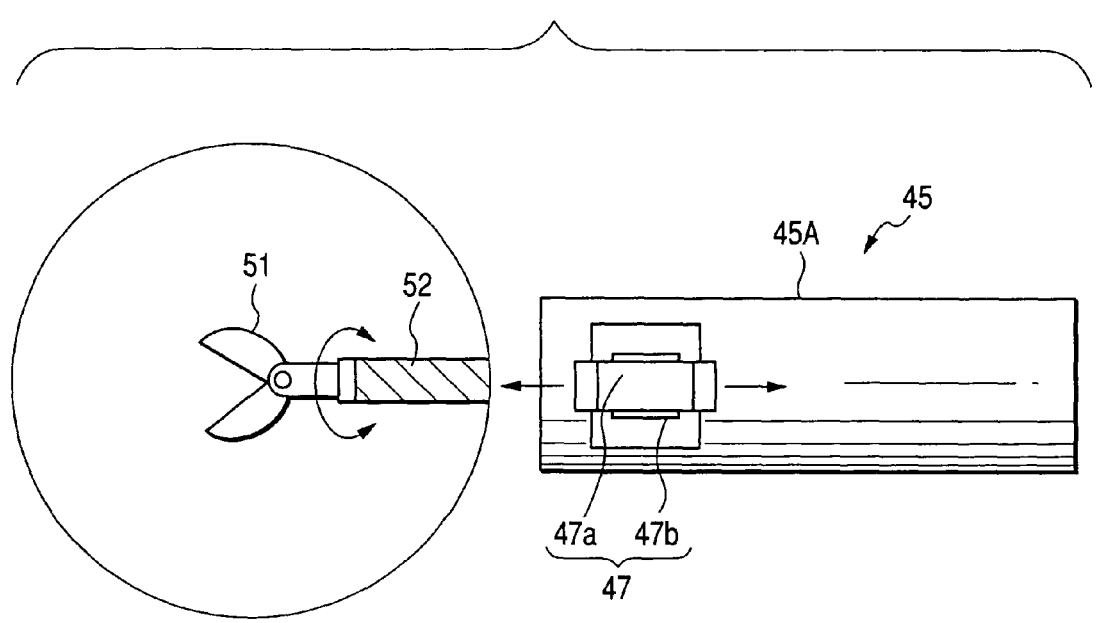
FIG. 12 is an illustration exemplifying rotational operations of the therapeutic instrument which are responsive to commands from the manipulating unit.

Meanwhile, as shown in FIG. 12, of the rotation commanding portion 47, when the operator operates the rotation lever 47a on the lever supporter 47b so that it tilts in the back and forth direction along the longitudinal axis of the manipulating unit 45, the sheath 52, i.e., the therapeutic instrument 50, can be rotated together with the therapeutic member 47b. In the present embodiment. In response to the forward rotation of the rotation lever 47a, the sheath 52 can be rotated counterclockwise together with the therapeutic member 51 when viewed along a direction from the base end of the therapeutic instrument 50 to the distal section thereof. In contrast, when tilting the rotation lever 47a backward, the sheath 52 can be rotated clockwise together with the therapeutic member 51 when viewed along a direction from the base end of the therapeutic instrument 50 to the distal section thereof.

Specifically, with the manipulating unit 45 gripped together with the insertion tube 11, the operator can operate the operation commanding portion 46 by, for example, the thumb. In response to such operations, the therapeutic instrument 50 can be moved back and forth and the therapeutic member 51 thereof can be opened and closed. Also the operator can operate the rotation commanding portion 47 by the first finger or others, so that the therapeutic member 51 can be rotated about the axis of the sheath 52.

More concretely, when the rotation lever 47a is tilted in either the backward direction or the forward direction, a command signal is supplied from the lever 47a to the instrument processor 20d via the so signal cable 45a. In reply to the command signal, the instrument processor 20d works to power the rotation motor 38 via the electric cable 38a so as to allow the motor 38 to rotate in the predetermined direction. The powered motor 38 rotates the gear 39 in the predetermined direction such that the gear 53a engaging with the gear 39 rotates the therapeutic instrument 50, Inserted in the therapeutic channel 11CH of the endoscope 10, about the axis thereof. The gear 39 is opposite to the gear 53a in their rotational directions, and the rotational direction of the motor 38 is opposite to the rotation in which the therapeutic instrument 50 is rotated.

The rotational force given to the sheath 52 is transmitted to the therapeutic member 51 attached to the distal end, so that the therapeutic member 51 is driven to rotate in the predetermine direction responsively to the forward tilt operation at the rotation lever 47a, while the therapeutic member 51 is driven to rotate in the direction opposite to the predetermine direction responsively to the backward tilt operation at the rotation lever 47a. The relationship between the tilt operating directions at the rotation lever 47a and the rotational directions of the therapeutic instrument 50 (including the sheath 52 and the therapeutic member 51) may be decided oppositely to the above relationship.

Further, the rotational speed of the therapeutic instrument 50 can be dependent on, how deep the rotation lever 47a is operated. In the present embodiment, by way of example, the rotational speed is faster as the operated tilt angle of the rotation lever 47a becomes larger.

Then various types of control for operating the therapeutic instrument 50, which is conducted by the instrument processor 20d (i.e. controller 20) according to the endoscope system 1, will now be exemplified. Incidentally, the following control examples consist of four examples and will be explained example by example in a separated manner, but the present invention is not limited to such a manner. Programs of the first to fourth control examples may be combined into one-program processing, in which those four programs are executed sequentially by the instrument processor 20d. Alternatively programs of any one or more control examples can be chosen or specified among the programs of the four control examples, and executed solely or in combination.

First Control Example

Referring to FIGS. 13-17, a first control example based on the first program shown in FIG. 13 will now be described, in which the sheath 52 of the therapeutic instrument 50 is inserted and pulled out in response to commands from the instrument processor 20d.

In response to operator's inserting or pulling-out operation for the therapeutic instrument 50 at the manipulating unit 45, the instrument processor 20d receives a command signal for the inserting or pulling-out operation from the unit 45 (FIG. 13, Step S11). The instrument processor 20d uses the received command signal to drive the instrument conveying unit 40 (Step S12), whereby the sheath 52 (together with the operating wire 52a) of the instrument 50 can be inserted or pulled out in or from the therapeutic channel 11CH.

Then the instrument processor 20d detects a bent state of the bendable section 11b of the insertion tube 11. (Step S13). To be specific, the detection is carried out the processor 20d receives, from the bending lever 15 of the operating base holder 12 of the endoscope 10, a command signal for bending the bendable section 11b and calculates the bent state of the bendable section 11b.

The instrument processor 20d uses information showing the bent state to control the rotational output of the motor 44 installed in the instrument conveying unit 40 when the therapeutic member 51 and sheath 52 pass through the bendable section 11b (Step S14). Concretely, depending on a bent angle (bent state) of the bendable section 11b, the rotational output of the motor 44, that is, an amount of power required by the roller 43a for driving the sheath 52, is corrected (increased or decreased) so that the sheath 52 (together with the operating wire 52a) can move smoothly at a constant speed through the therapeutic channel 11CH. In this case, therefore, the processing at Step S15 establishes the correcting means in the instrument processor 20d.

The bent state will now be detailed. As shown in FIG. 14, in cases where the insertion tube 11 is almost in a straight state (i.e., not bent), the therapeutic channel 11CH is also substantially straight. Hence friction resistance between the therapeutic channel 11CH and the sheath 52 is smaller, so that the power amount necessary for conveying the sheath 52 by the roller 43a is also smaller.

Figure 15:
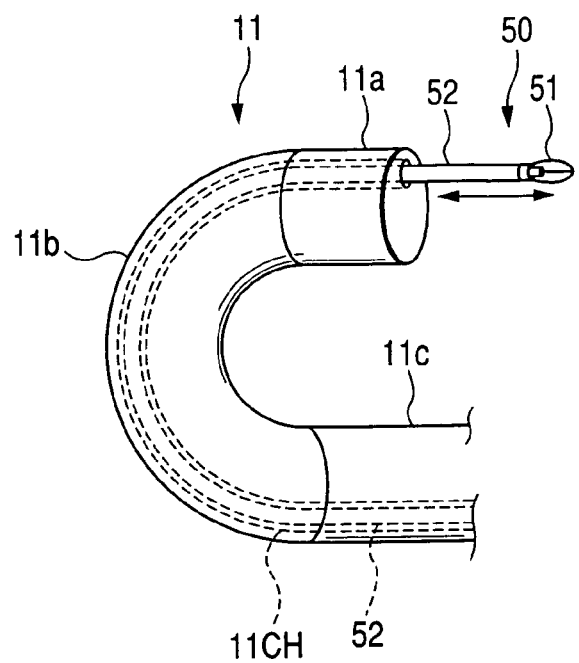
FIG. 15 is an illustration explaining how the therapeutic instrument is conveyed through the insertion tube which is bent at a certain angle.

In contrast, as shown in FIG. 15, when the bendable section 11b is bent in any direction, the therapeutic channel 11CH is in a bent state. Hence the friction resistance between the sheath 52 and the therapeutic channel 11CH is obliged to be larger than that in a case where the therapeutic channel 11CH is straight extended. That is, the larger the bent angle of the bendable section 11b, the larger the friction resistance. Accordingly, the power amount necessary for conveying the sheath 52 by the roller 43a of the instrument conveying unit 40 becomes larger with an increase in the bent angle of the bendable section 11b.

Figure 16:
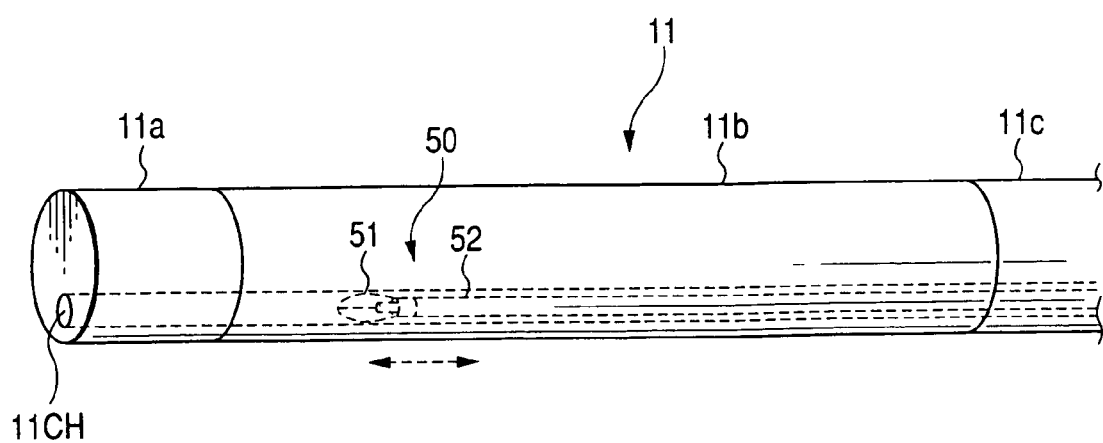
FIG. 16 is an illustration explaining how the therapeutic instrument is conveyed through the insertion tube which is almost linearly extended.
Figure 17:
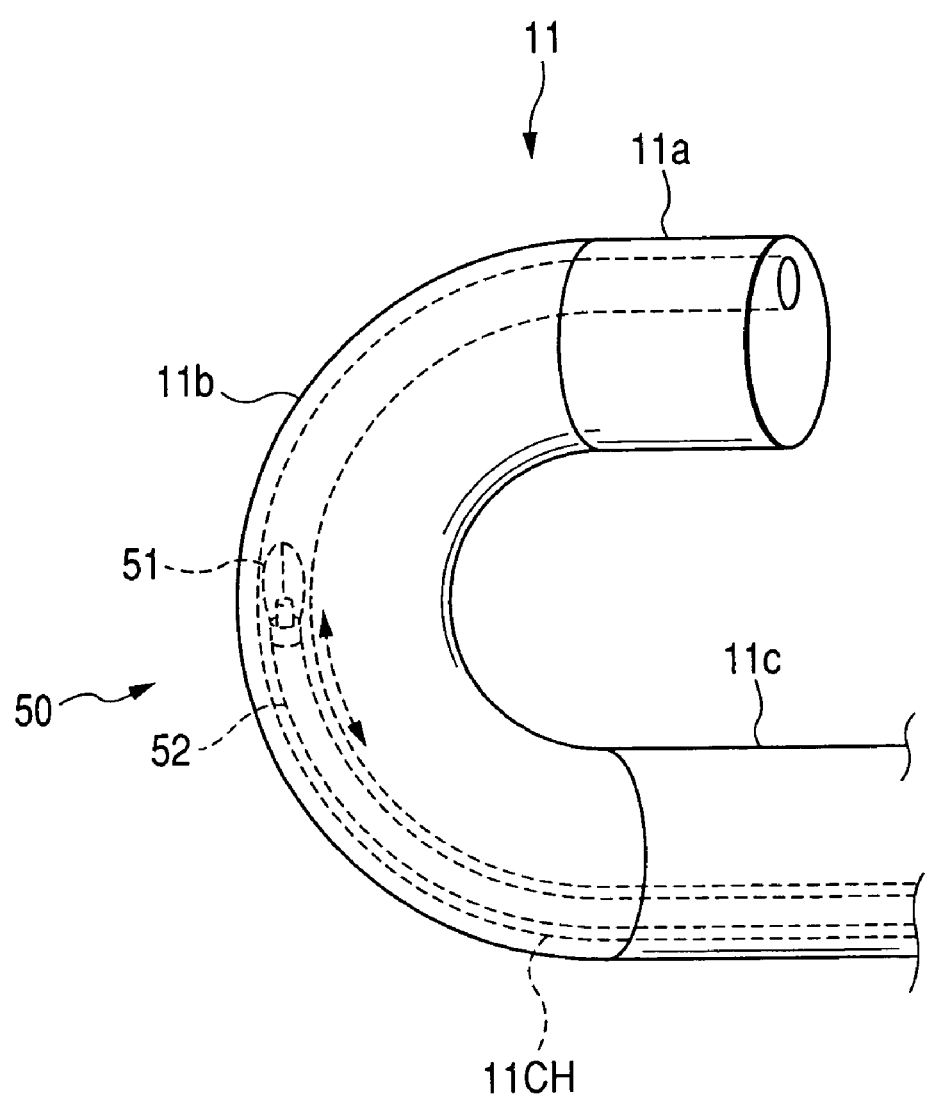
FIG. 17 is an illustration explaining how the therapeutic instrument is conveyed through the insertion tube which is bent at a certain angle.

This relationship between the bent angle and the friction resistance is also true of the therapeutic member 51 passing the bendable section 11b which is in a bent state. FIG. 16 illustrates a state where the therapeutic member 51 passes the bendable section 11b which is straight extended, while FIG. 17 illustrates another state where the therapeutic member 51 passes the bendable section 11b which is in a bent state. Thus the power amount for conveying the sheath 52 necessary when the bendable section 11b is bent should be larger than that necessary when the bendable section 11b is straight extended. Accordingly, even in this case, the power amount necessary for conveying the sheath 52 by the roller 43a of the instrument conveying unit 40 becomes larger with an increase in the bent angle of the bendable section 11b.

As stated above, in the endoscope system 1 according to the present embodiment, the instrument processor 20d functionally realizes the correction means by conducting the first program. And depending on the bent angle of the bendable section 11b, the rotation output to be outputted from the roller 43a of the instrument conveying unit 40 is corrected (changed or controlled). In the present endoscope system 1, even when an operator may operate the manipulating unit 45 in the same way at the same speed so as to create a constant operation command signal, the power amount necessary for conveying the sheath 52 is corrected to increase or decrease the amount in accordance with the bent state of the bendable section 11b. Thus an interval of time during which the therapeutic member 51 reaches the distal section 11a and an interval of time during which the therapeutic member 51 appears or disappears from or in the front of the distal section 11a can be kept at a constant amount (that is, at the same speed). In other words, with the operation lever 46a on the manipulating unit 45 kept at a constant tilt angle, the response in making the sheath 52 move back and forth can be maintained at a constant time whenever the bendable section 11b is operated to have any bent angle.

Second Control Example

Figure 18:
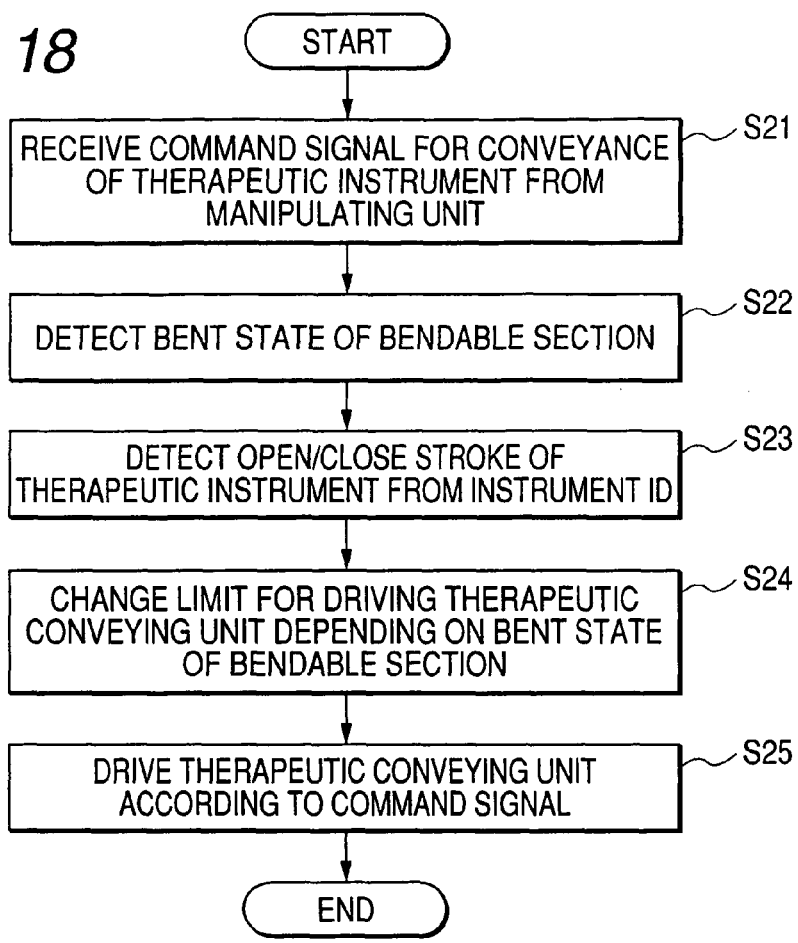
FIG. 18 is a flowchart explaining a second program executed by the controller when a therapeutic member of the therapeutic instrument is required to open and close.
Figure 19:
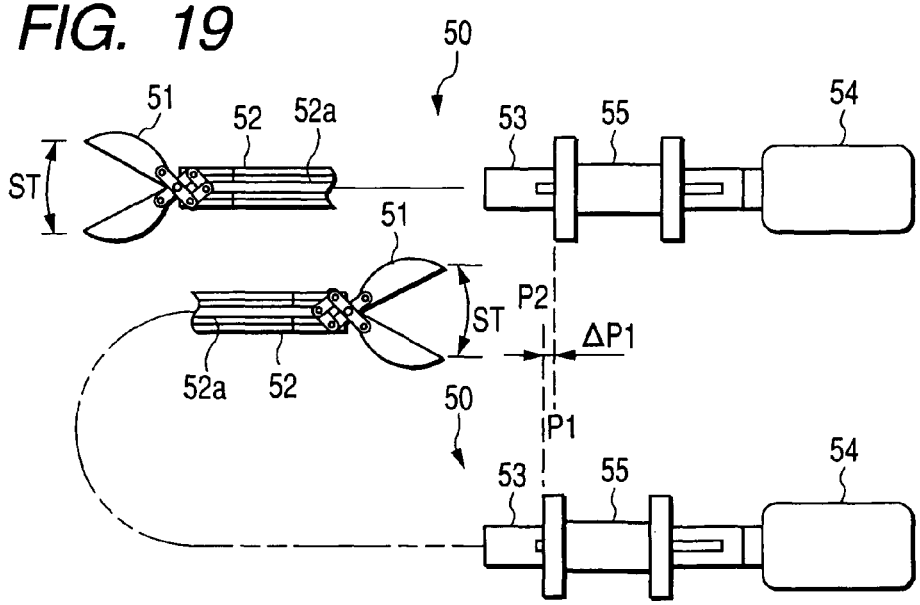
FIGS. 19 and 20 are plan views each explaining play due to the open/close operations of the therapeutic member comparatively between a state where a therapeutic channel is straight and a state where the therapeutic channel is bent.
Figure 20:
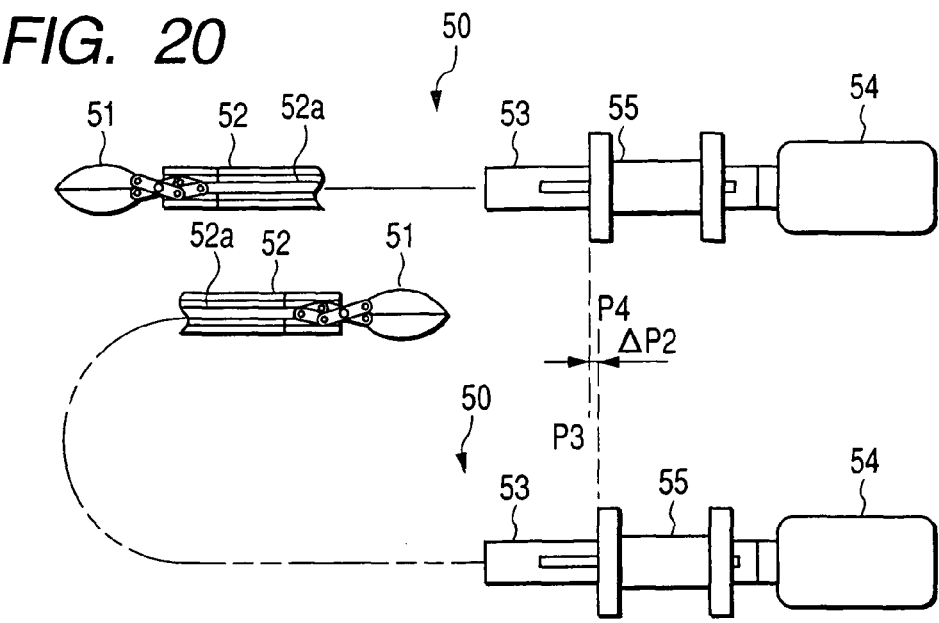

Referring to FIGS. 18-20, a second control example based on the second program shown in FIG. 18 will now be described, in which the therapeutic member 51 of the therapeutic instrument 50, which is for example a clamping forceps, is opened and closed in response to commands from the instrument processor 20d. In this example, the same or similar processing as or to the processes in the first program will be simplified or omitted in their description.

In the present example, limits are given to open/close strokes of the therapeutic member 51, member by member. The instrument processor 20d reads out, from the therapeutic instrument ID of the therapeutic instrument 50, the open/close stroke which is set thereto and, based on the ID information, controls a rotation limit to which the rotation of the motor 63 of the instrument operating unit 30 is limited. Hence, so as not to tract and relax the operating wire 52a that opens and closes the therapeutic member 51 more than the limit stroke, the amount of movement of the slider 55 is limited. The open/close stroke is read from information indicative of the therapeutic instrument ID.

In some bent states of the bendable section 11b, when the operating wire 52a is subject to traction and relaxation to provide the therapeutic member 51 with its open/close stroke, there are caused errors of the amounts of traction and relaxation due to a slight amount of play. Specifically, when the sheath 52 is bent, the operating wire 52a passing the bent portion causes play, resulting in that only a larger amount of traction may completely close the therapeutic member 51. This incomplete close may cause a decrease in the gripping force for a target in a body cavity. Taking this situation into account, the instrument processor 20d of the endoscope system 1 conducts the processing on a second program.

As shown in FIG. 18, in response to the input of an operation command signal for the therapeutic instrument 50, which comes from the manipulating unit 45 (Step S21), the instrument processor 20d detects the bent state of the bendable section 11b (Step S22), which is followed by detecting an open/close stroke ST (refer to FIG. 19) from information about the therapeutic instrument ID (Step S23). In the present invention, the limit of traction/relaxation of the operating wire 42a is decided based on an open/close stroke ST amount obtained when the sheath 52 is regarded as being almost straight extended. The limits are decided as maximum slidable amounts allowed to the slider 55 of the handle 53 in a state where the sheath 52 is almost linearly extended.

Depending on the information indicative of the current bent state of the bendable section 11b, the instrument processor 20d changes (corrects) the limit for the detected open/close stroke realized by the drive of the instrument operating unit 30 (Step S24). The reason for the change (correction) of the limit lies in that, when the bendable section 11b is bent, i.e., the sheath 52 is also bent, a predetermined open/close stroke to be performed by the operating wire 52a should be kept to completely close the instrument member 51, regardless of how much the bendable section 11b has been bent. Thus, a rotational limit to be given to the motor 36 of the instrument operating unit 30 is increased to raise, in a controlled manner, a limit to move the slider 55 of the handle 53. The processing at Step S24 corresponds to the correcting means functionally realized by the instrument processor 20d.

For example, FIG. 19 provides two typical states of the same therapeutic instrument 50; in one state (upper), the sheath 52 is almost linearly extended, so that the therapeutic member 50 is opened to have a predetermined open angle (in this case, its limit angle), while in the other state (lower), the sheath 52 is bent according to a predetermined bent state of the bendable section 11b, so that the therapeutic member 51 is opened to have the same predetermined open angle. In both cases, there is a difference between the head end positions of the slider 55 on the handle 53. That is, as illustrated in FIG. 19, the former state provides the head position of the slider 55 shown by a dashed line P1, whilst the latter state provides the head position of the slider 55 shown by a dashed line P2 which is located ahead of the dashed line P1.

When assuming that there is a distance difference P1 between the dashed lines P1 and P2 in the axial direction of the handle 53, this distance difference P1 leads to a small amount of play. To avoid this play, as stated, the instrument processor 20d increases the rotational limit for the motor 36, which results in a correction relaxing the operating wire 52a. This allows the position P2 to axially move back so that an equi-positional state of P2=P1 can be established.

Another example is shown in FIG. 20, where there are provided two typical states of the same therapeutic instrument 50; in one state (upper), the sheath 52 is almost linearly extended, so that the therapeutic member 50 is closed to have a predetermined close angle (in this case, another limit angle), while in the other state (lower), the sheath 52 is bent according to a predetermined bent state of the bendable section 11b, so that the therapeutic member 51 is closed to have the same predetermined close angle. In both cases, there is a difference between the head end positions of the slider 55. That is, as illustrated in FIG. 20, the former state provides the head position of the slider 55 shown by a dashed line P3, whilst the latter state provides the head position of the slider 55 shown by a dashed line P4 which is located at the rear of the dashed line P3.

When assuming that there is a distance difference ΔP2 between the dashed lines P3 and P4 in the axial direction of the handle 53, this distance difference ΔP2 leads to a small amount of play. To avoid this play, as stated, the instrument processor 20d increases the rotational limit for the motor 36, which results in the correction that pulls the operating wire 52a. This allows the position P4 to axially move forward so that an equi-positional state of P4=P3 can be established.

Accordingly, in the endoscope system adopting the foregoing second program, regardless of the fact that the bendable section 11b is bent at which angle, the therapeutic member 51 can be opened and closed at a predetermined constant open/close stroke. Namely, even when the operator operates the bendable section 11b by manually manipulating the operation lever 46a by a predetermined tilt amount in the right or left direction of the manipulating unit 45, the therapeutic member 51 can always be opened and closed at the predetermined same constant stroke ST corresponding to the predetermined tilt amount operated.

Third Control Example

Figure 21:
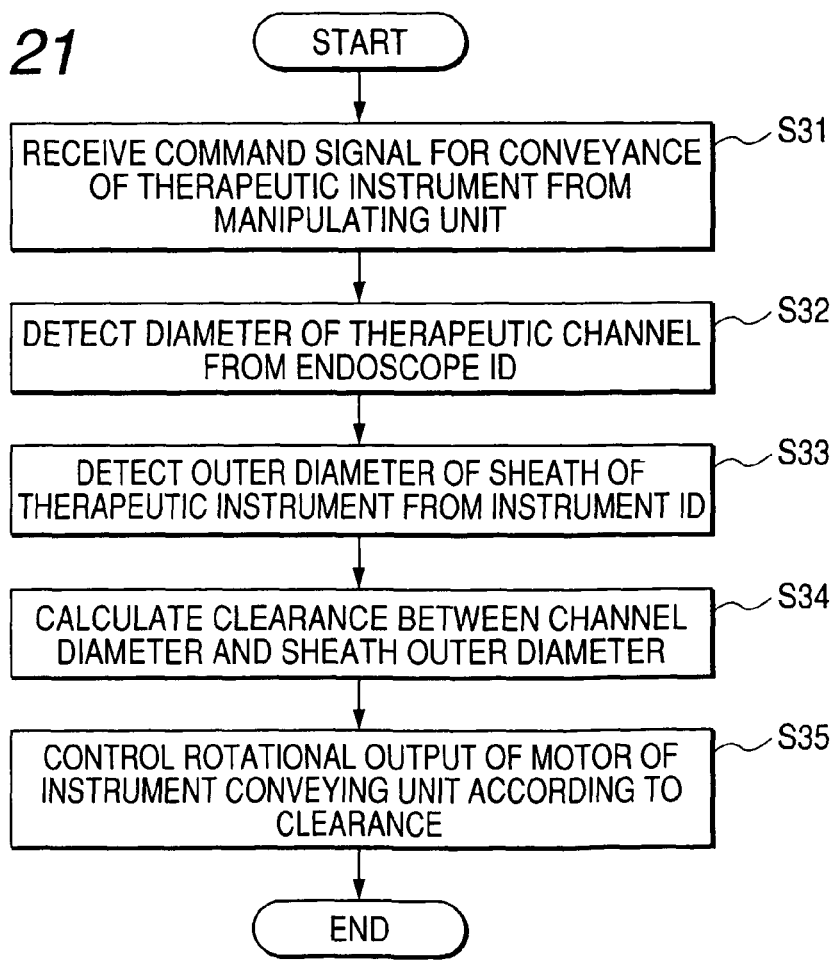
FIG. 21 is a flowchart explaining a third program executed by the controller when the therapeutic instrument is required to be inserted and pulled out.
Figure 32:
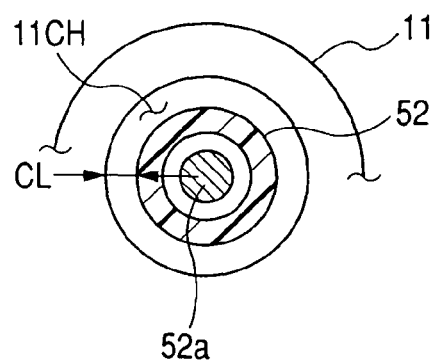
FIG. 32 explains a clearance made between the insertion tube and the sheath inserted in through the insertion tube.

Referring to FIGS. 21 and 32, a third control example based on the third program shown in FIG. 21 will now be described, in which the amount of power necessary for conveying (inserting or pulling back) the sheath 50 (together with the operating wire 52a) by the instrument conveying unit 40. In this example, the control is made with taking into account differences among the diameters of therapeutic channels and differences among the diameters of sheaths. This is because differences of the types of endoscopes are reflected in differences of the diameters of the therapeutic channels thereof and differences of the types of therapeutic instruments are reflected in differences of the outer diameters of sheaths thereof.

The third program, which is shown in FIG. 21, is executed by the instrument processor 20d, in which, first of all, the instrument processor 20d receives, from the manipulating unit 45, a command signal for conveying the therapeutic instrument 50 (Step S31). Responsively to this signal reception, the processor 20d detects information indicative of the diameter of the therapeutic channel 11CH from the endoscope ID given to the endoscope 10 (Step S32), then detects information indicative of the outer diameter of the sheath 52 from the instrument ID given to the therapeutic instrument 50 (Step 33).

The endoscope processor 20d then calculates a clearance CL (refer to FIG. 32) between the outer diameter of the sheath 52 and the diameter of the therapeutic channel 11CH (Step S34). Depending on the calculated clearance CL, the processor 20d controls the rotational output of the motor 44 mounted at the instrument conveying unit 40 to adjust the conveyance speed of the sheath 52 (Step S35).

Practically, in cases where the above clearance CL is smaller than a predetermined amount, the friction resistance caused between the therapeutic channel 11CH and the sheath 52 becomes larger according to the smallness of the clearance CL, the instrument processor 20d commands a rise in the power amount for the conveyance outputted from the instrument conveying unit 40. In contrast, when the clearance CL is larger or equal to the predetermined amount, the friction resistance is lower. Thus the processor 20d commands a drop in the power amount for conveyance outputted from the instrument conveying unit 40.

Thus, in a case where the constant command having the same amount for conveyance of the sheath 52 is issued from the manipulating unit 45, by the instrument processor 20d, the rotational output of the motor 44 mounted on the instrument conveying unit 40 is corrected (changed) to permit the sheath 52 is conveyed (inserted or pulled out) at a constant speed which is the same even if the clearance CL varies. In this correction of the power amount for the conveyance, the relationships between the diameters of various types of therapeutic channels and the outer diameters of various types of sheaths are utilized. The processing at Step S35 composes the correction means functionally carried out by the instrument processor 20d.

Accordingly, in the endoscope system 1 according to the present embodiment, the third program, which is carried out by the instrument processor 20d, allows the sheath 52 is conveyed (inserted or pulled back) at a constant speed, irrelevantly of the outer diameter of the sheath 52 of a therapeutic instrument 50 to be used and the diameter of the therapeutic channel 11CH of an endoscope 10 to be used, as long as the same-amount constant command for conveyance is issued from the manipulating unit 45. Even when different types of endoscopes 10 are used and/or different types of therapeutic instruments 50 are used, it is therefore possible for operators to remove an uncomfortable feeling from their operations to insert and pull back the sheath 52 (together with the operating wire 52a).

As a modification, the above third program may be performed in such a manner that the amount of power from the instrument conveying unit 40 is controlled on such factors as material types and hardness of the therapeutic channel of each endoscope and the sheath of each therapeutic instrument, solely or in combination with the foregoing diameter relationship.

Fourth Control Example

Figure 22:
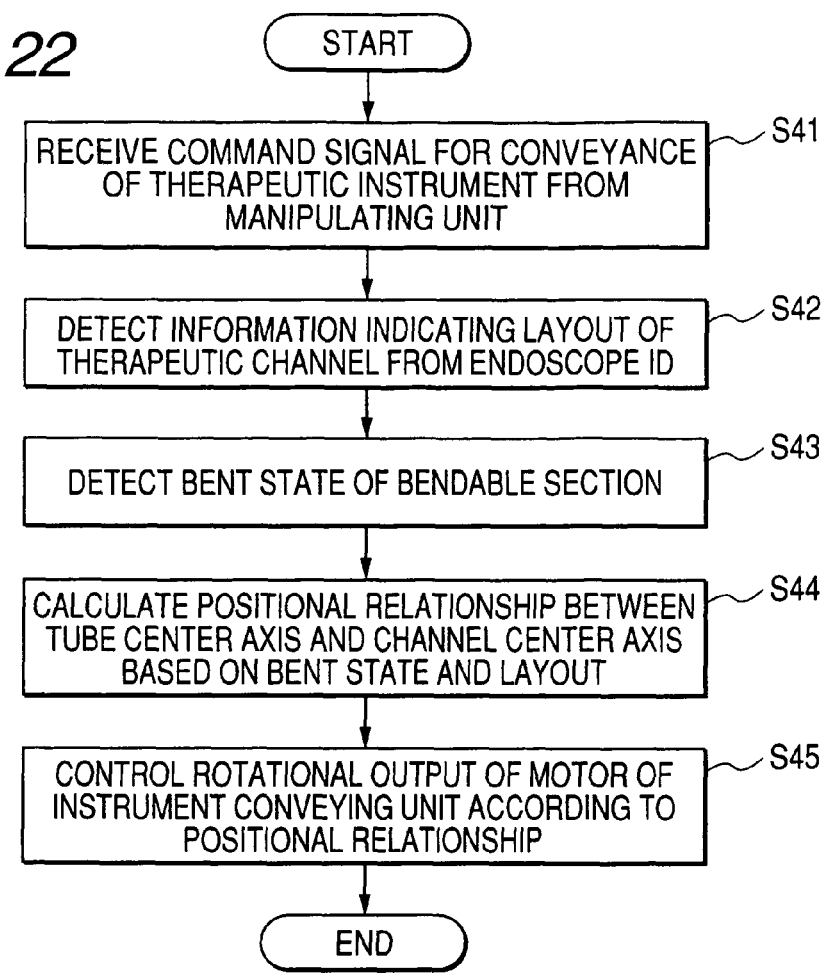
FIG. 22 is a flowchart explaining a fourth program executed by the controller when the therapeutic instrument is required to be inserted and pulled out.

Referring to FIGS. 22-30, a fourth control example based on the fourth program shown in FIG. 22 will now be described, in which the fourth program is executed by the instrument processor 20d when a variety of types of therapeutic instruments 50 are employed for conveying their sheaths 52.

Different types of endoscopes have different arrangements of therapeutic channels formed through their insertion tubes, respectively, and also different arrangements of openings in the fronts of the distal sections of the therapeutic channels, respectively. Thus, depending on (i) the type of the endoscope 10, (ii) how deep the bendable section 11b is bent, or (iii) in which direction the bendable section 11b is bent, how deep the therapeutic channel 11CH in the bendable section 11b is bent is influenced. With considering this fact, the fourth program according the present example is set to allow the sheath 52 to move at the same constant speed, even if an endoscope 10 whose therapeutic channel 11CH formed in the front of its distal section is positionally different from the others.

The forth program exemplified in FIG. 22 is performed by the instrument processor 20d. In reply to an operator's operation, a command signal for conveying the therapeutic instrument 50 is issued from the manipulating unit 45 and received by the processor 20d (Step S41). Then, using the endoscope ID of the endoscope 10, a piece of information indicative of the layout of the therapeutic channel 11CH is detected (Step S42).

Figure 23:
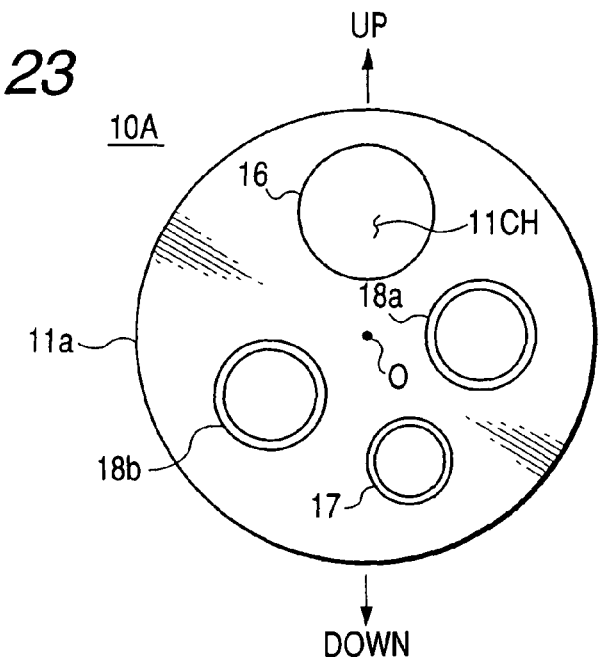
FIG. 23 is a front view showing an end surface of a distal section of the insertion tube adopted by a first type of endoscope.
Figure 24:
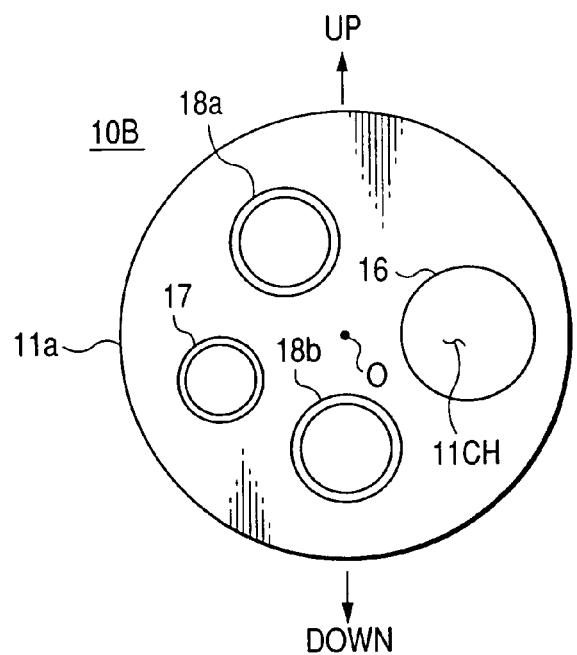
FIG. 24 is a front view showing an end surface of a distal section of the insertion tube adopted by a second type of endoscope.

The layouts are exemplified in FIGS. 23 and 24, which illustrate views of the frontal surfaces of distal sections 11a of two types of endoscopes 10A and 10B, respectively. In each front shown in each of FIGS. 23 and 24, compared to the upward and downward directions (UP, DOWN) in which the bendable sections 11b are bent, an opening 16 of the therapeutic channel 11CH is arranged positionally differently from that of the other type of endoscope 10A (10B). That is, the arrangement of the opening 16 differs type by type. In the example shown in FIG. 23, the opening 16 is arranged off-centered (bounced off from the center O in the front) and closer to the periphery of the front in the upward direction in which the bendable section 11b is bent. In contrast, in the other example shown in FIG. 24, the opening 16 is arranged off-centered (bounced off from the center O in the front) and closer to the periphery of the front in a lateral direction (in the drawing, rightward) perpendicular to the upward/downward direction.

The layout type is not limited to those two types. Incidentally the therapeutic channel 11CH becomes almost straight through the insertion tube 11 of the endoscope 10, whenever the insertion tube 11 is extended straight. In FIGS. 23 and 24, a reference 17 is an imaging optical system constituting part of imaging means and references 18a and 18b show illuminating optical systems composing part of illumination means.

Returning to FIG. 22, the instrument processor 20d detects information indicating a bent state of the bendable section 11b of the endoscope 10A (10B) currently used (Step S43). Then, using the information indicating the bent state of the bendable section 11b and the layout between the therapeutic channel 11CH and the opening 16, the processor 20d calculates a relationship between an axis (i.e., tube center axis) of the endoscope 10A (10B) and a channel center axis (a center axis of the therapeutic channel 11CH) (Step S44).

And, based on the calculated results, that is, the relationship between the tube center axis and the channel center axis, the rotational output of the motor 44 mounted on the instrument conveying unit 40 is changed (corrected) (Step S45). The processing at Step S45 thus composes the correcting means functionally realized by the instrument processor 20d.

Figure 25:
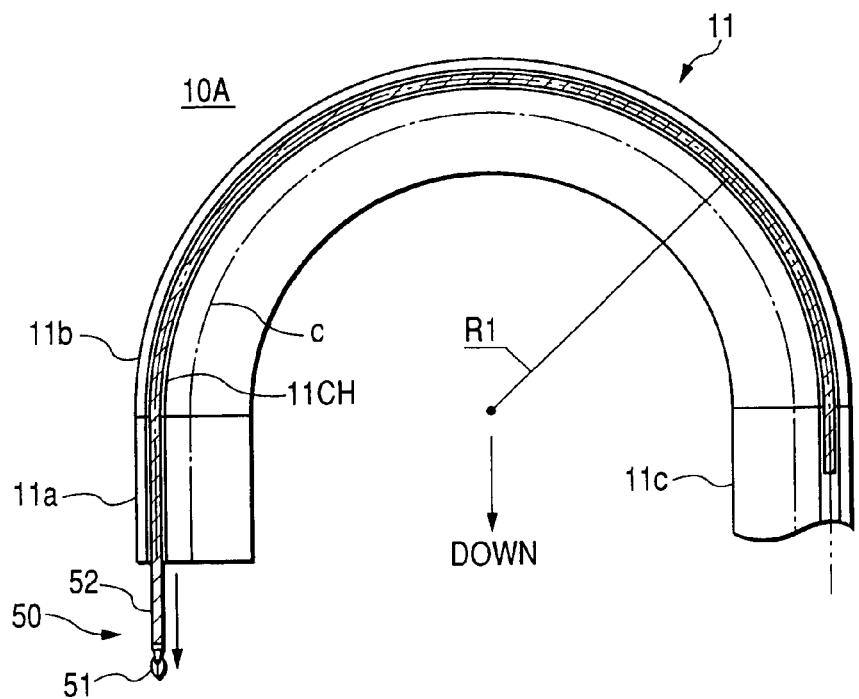
FIG. 25 is a longitudinal sectional view showing the distal section of the insertion tube employed by the first type of endoscope, the view explaining the operations in conveying the therapeutic instrument.
Figure 26:
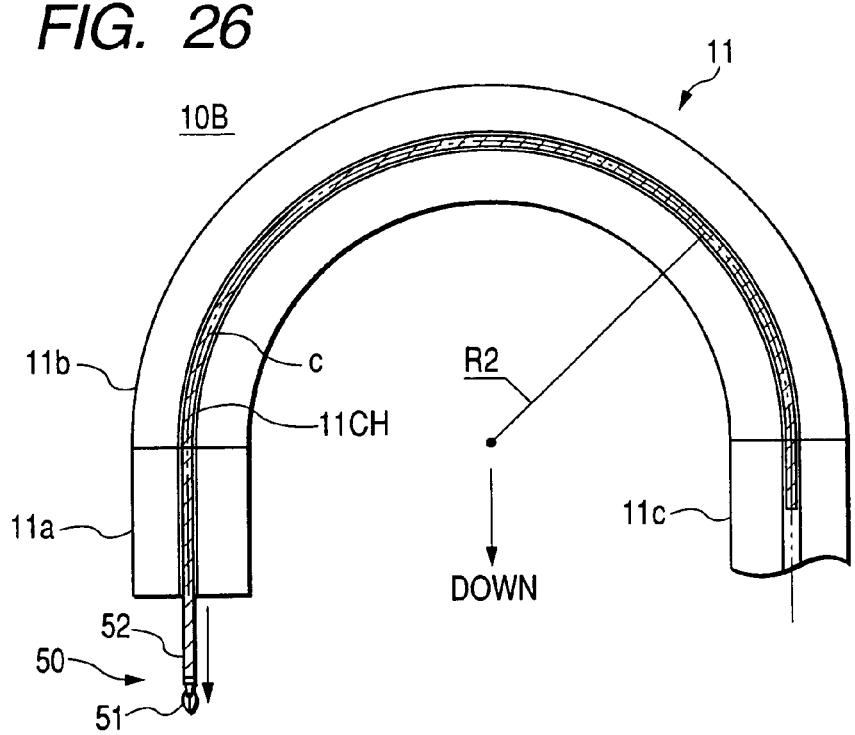
FIG. 26 is a longitudinal sectional view of the distal section of the insertion tube employed by the second type of endoscope, the view explaining the operations in conveying the therapeutic instrument.

Concrete examples of the above correction will now be described with reference to FIGS. 25 and 26 as well as FIGS. 23 and 24 showing the different layouts as described. FIG. 25 shows part of the first endoscope 10A having the layout of the therapeutic channel 11CH and the opening 16 shown in FIG. 23, while FIG. 26 does part of the second endoscope 10B having the layout of the therapeutic channel 11CH and the opening 16 shown in FIG. 24.

As shown in FIG. 25, in a case where the bendable section 11b of the first endoscope 10A is bent in the bending downward (DOWN) direction, the therapeutic channel 11CH is forced to be located on the radially outward direction than the tube center axis C of the first endoscope 10. However, as shown in FIG. 26, in a case where the bendable section 11b of the second endoscope 10B is bent in the bending downward (DOWN) direction, the therapeutic channel 11CH is forced to be located on and along the tube center axis C of the first endoscope 10.

Thus, in relation to a bent state (of which curvature radius is R1) of the therapeutic channel 11CH of the first endoscope 10A, the therapeutic channel 11CH of the second endoscope 10B presents a bent state of which curvature radius is R2 smaller than R1 (R2<R1). The sheath 52 encounters a larger amount of resistance when it moves along the therapeutic channel 11CH of the second endoscope 10B, compared to that for the first endoscope 10A.

With taking this situation into account, the instrument processor 20d in the second endoscope 10B issues a correction signal commanding a rise in the rotation output of the motor 44 on the instrument conveying unit 40, so that the amount of power for conveying the sheath 52 in the second endoscope 10B is raised more than that for the first endoscope 10A. In this control, the processor 20d also performs speed control such that the conveying speed of the sheath 52 becomes almost the same between the first and second endoscopes 10A and 10B.

On the contrary, in a case where the bendable section 11b is bent in the bending upward (UP) direction in each of the first and second endoscopes 10A and 10B, compared to a bent state (of which curvature radius is R2) of the therapeutic channel 11CH of the second endoscope 10B, the therapeutic channel 11CH of the first endoscope 10A presents a bent state of which curvature radius is R1 smaller than R2 (R1<R2).

In this case, the instrument processor 20d in the first endoscope 10A commands a rise in the amount of power for conveying the sheath 52 (i.e., the rotational output of the motor 44), which is supplied from the instrument conveying unit 40, compared to the case for the second endoscope 10B, so that the sheath 52 is conveyed at the constant same speed.

Hence, the fourth program, performed by the instrument processor 20d, permits the sheath 52 to move at the same constant speed, independently of which type of endoscope 10A or 10B is used, that is, independently of how the therapeutic channel 11CH and the opening 16 are layout in the front, provided that a constant signal commanding the predetermined same speed conveyance is issued from the manipulating unit 45. As a result, even when an endoscope being used is changed to another one, an operator can be avoided from having an uncomfortable feeling in inserting and pulling out the sheath 52 (together with the operating wire 52a) of the therapeutic instrument 50.

In this forth control example, as described, the two types of endoscopes 10A and 10B have been adopted to explain their layouts of the therapeutic channels 11A and the openings 16. And, the fourth control includes the step of reading out the information indicating their layouts from the endoscope IDs and controls the conveyance of the sheath 52 at a constant specified speed.

The forth control example may be modified to a system that employs one endoscope 10. In even the one endoscope 10, the position at which the sheath 52 passes may depend on the diameter of the therapeutic channel 11A. For example, as shown in FIGS. 27 and 28, the sheath 52 is inserted or pulled back through the therapeutic channel 11CH at different positions therein, in cases where the diameter of the therapeutic channel 11CH is larger than the outer diameter of the conveyed sheath 52.

Figure 27:
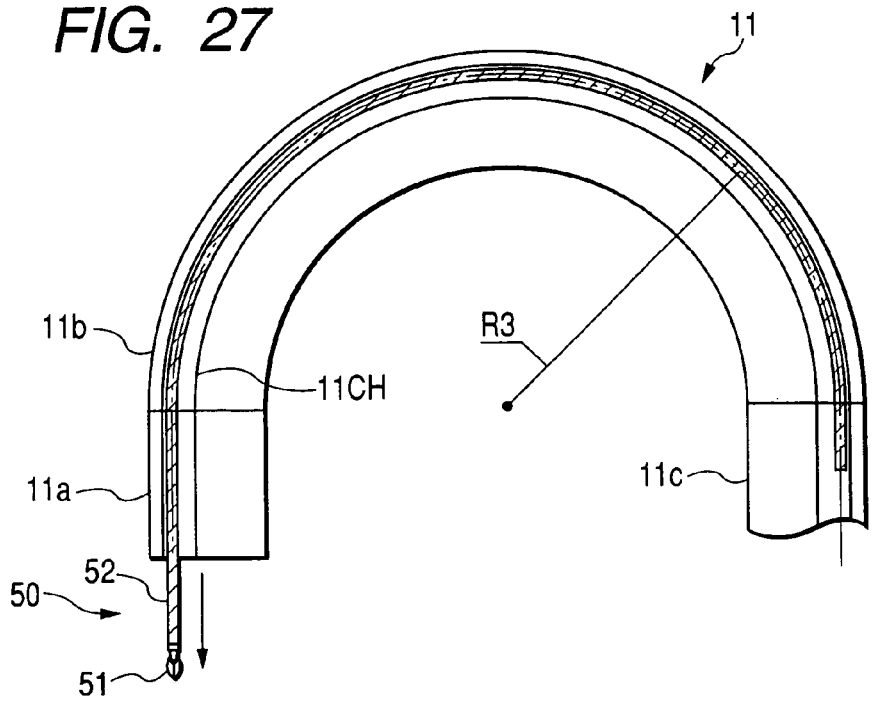
FIGS. 27 to 30 are longitudinal sectional views each showing the as distal section of the insertion tube employed by the endoscope, the view explaining the operations in conveying the therapeutic instrument.
Figure 28:
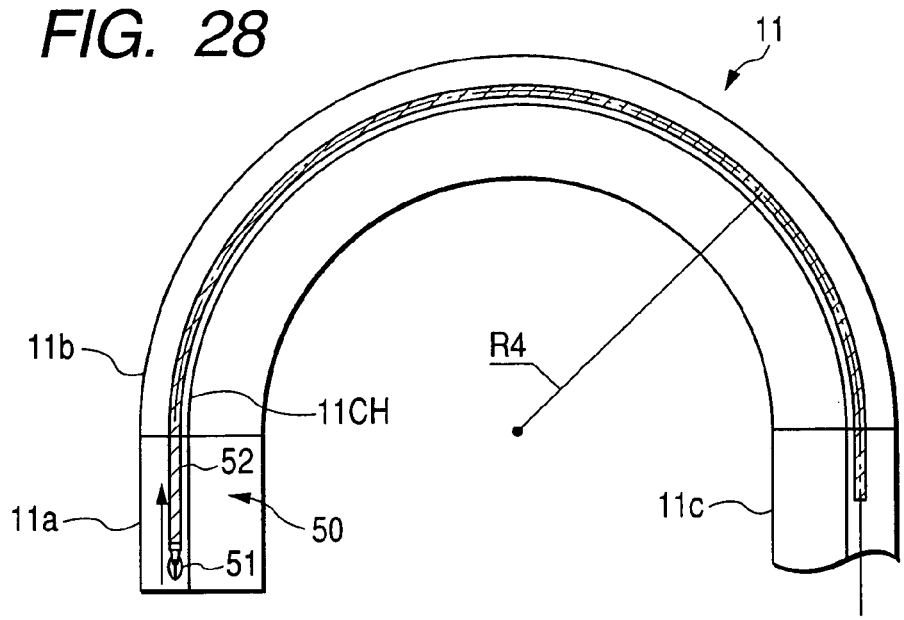

Specifically, in the case of FIG. 27 where the sheath 52 is conveyed to be inserted, the sheath 52 passes along the outside inner wall of the therapeutic channel 11CH so as to represent a larger curvature radius R3. In the case of FIG. 28 where the sheath 52 is conveyed to be pulled back, the sheath 52 passes along the inside inner wall of the therapeutic channel 11CH so as to represent a smaller curvature radius R4 (<R3).

Therefore, the instrument processor 20d operates to detect, from the endoscope ID, bits of information indicative of the diameter of the therapeutic channel 11CH and the outer diameter of the sheath 52, uses the information to calculate a clearance between both diameters, and controls the conveyance speed of the sheath 52 at a constant specified value by adjusting the rotational output of the motor 44 depending on the calculated clearance, in the same way as Steps S32-S35 in FIG. 21. That is, the processor 20d is in charge of controlling changes in the amount of power necessary for inserting and pulling out the sheath 52 (together with the operating wire 52a placed therethrough) so that the conveyance speed is kept at the constant specified value.

Figure 29:
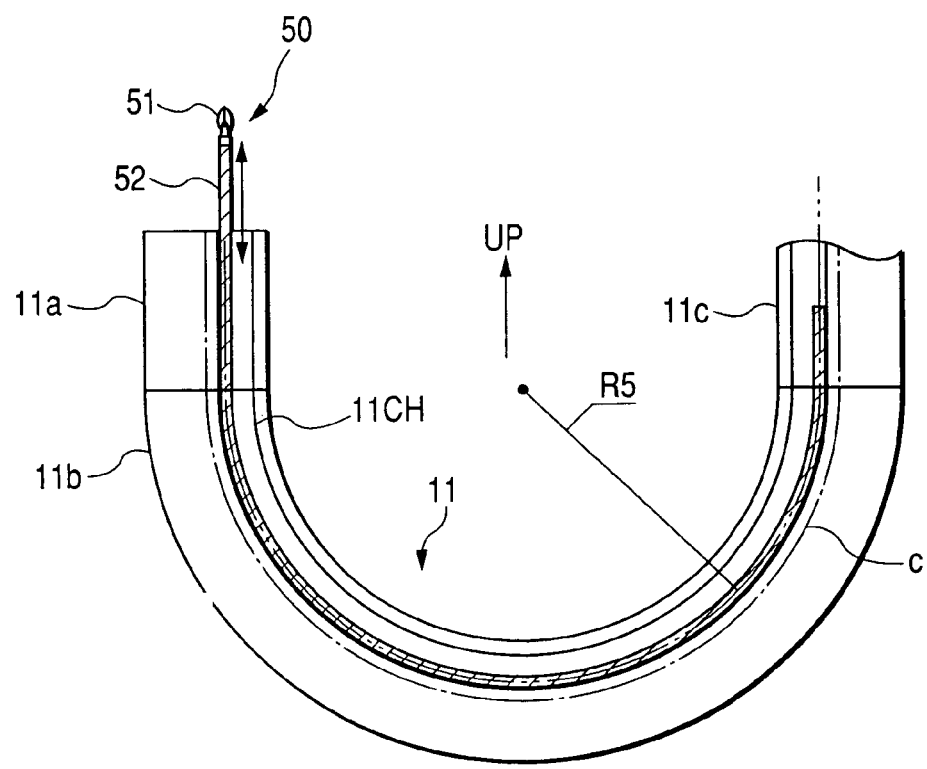
Figure 30:
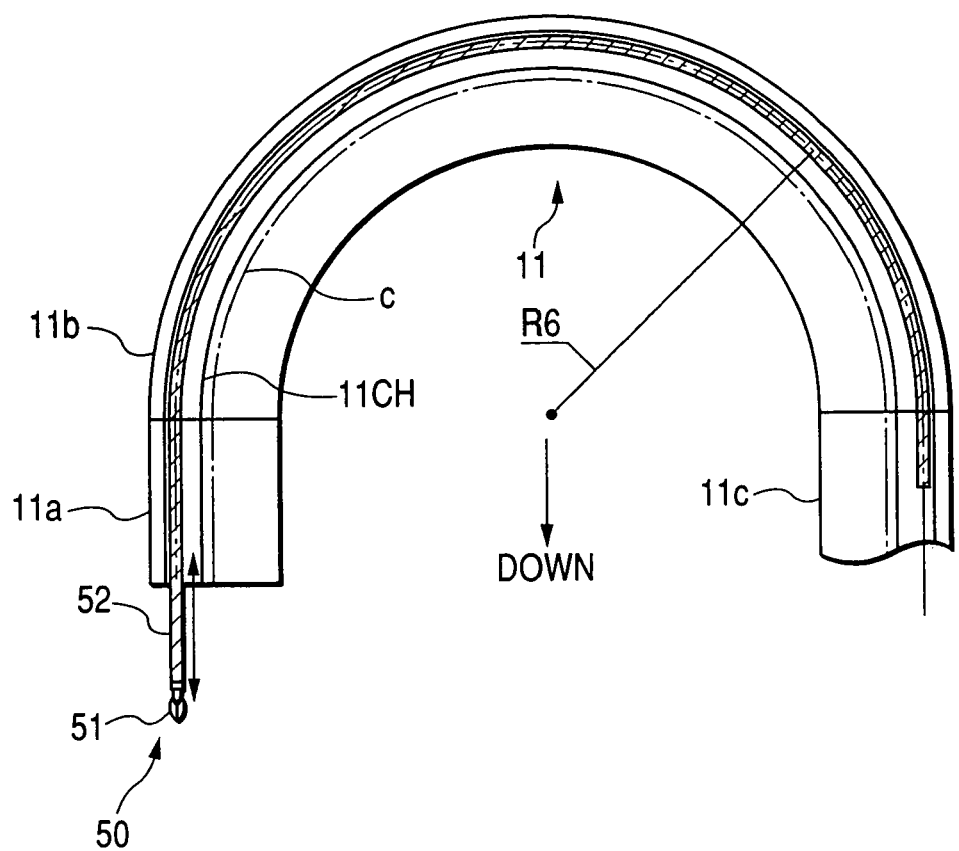

Another modification is concerned with one endoscope 10A (refer to FIG. 23) whose layout of the therapeutic channel 11CH influences the bent states thereof when the bendable section 11b is bent upward or downward. For example, as shown in FIG. 29, when the bendable section 11b is bent upward, the therapeutic channel 11CH is located radially inside the tube center axis C in the channel 11CH. By contrast, as shown in FIG. 30, when the bendable section 11b is bent downward, the therapeutic channel 11CH is located radially outside the tube center so axis C In the channel 11CH.

When the bendable section 11b is bent upward (UP) so that the sheath 52 passes therethrough to represent a curvature radius R5 and bent downward (DOWN) so that the sheath 52 passes therethrough to represent a curvature radius R6, a relationship of R5<R6 is realized. Thus, due to an upward bend of the bendable section 11b, the resistance caused in conveying the sheath 52 becomes larger in amounts than that caused in bending it downward.

The instrument processor 20d controls the rotational output from the motor 44 of the instrument conveying unit 40 so as to raise the rotational output when the bendable section 11b is bent upward, more than that when the bendable section 11b is bent downward. Hence the sheath 52 can be inserted and pulled out at a specified speed which is almost constant. Incidentally, in the above description of the control, it is premised that the bent angles in the upward and downward directions are equal to each other.

In summary, the endoscope system 1 according to the present embodiment performs the foregoing various programs. When the insertion tube 11 of the endoscope 10 is subjected to operations to bend its bendable sections 11b at any angle and/or in any direction, it is possible for operators to not only convey (insert and pull out) the sheath 52 (together with the operating wire 52a inserted therethrough) of the therapeutic instrument 50 but also open and close the therapeutic member 51 of the therapeutic instrument 50 with almost the same response feeling, whereby operationality is improved.

As a modification, a sensor sensing leakage of water may be installed to the therapeutic channel 11CH. In this case, a sensed signal from the sensor is provided to the instrument processor 20d, with the result that the processor calculates a value of resistance between the channel 11CH and the sheath 52 to use the calculate values to correct the amount of power generated by the instrument conveying unit 40. If the water leakage occurs, the resistance between the channel 11CH and the sheath 52 becomes smaller. In this case, the processor 20d lowers the amount of power for conveying the sheath 52 (with the operating wire 52a), which is generated by the unit 40, with the aim of keeping the conveyance speed of the sheath 52 at an almost predetermined constant value.

Although the description above contains many specificities, these should not be construed as limiting the scope of the invention but as merely providing illustrations of some of the presently preferred embodiments of the present invention. Thus the scope of the present invention should be determined by the appended claims.

What is claimed is:

1. An endoscope system comprising:
    an endoscope comprising an elongated flexible insertion tube having a distal end accommodating therein at least an imaging optical system and having a flexibly bendable section juxtaposed to the distal end, the insertion tube being inserted into an object being examined;
    a medical instrument used in combination with the endoscope and inserted into the object through the insertion tube inserted into the object, the medical instrument having a therapeutic member;
    an operating unit manually operated by an operator to command both an inserting and pulling-out operation of the medical instrument and a therapeutic operation of the therapeutic member of the medical instrument;
    a first drive unit configured to drive the medical instrument to perform the inserting and pulling-out operation thereof in response to an operator's operation performed with the operating unit;

a second drive unit configured to drive the medical instrument to perform the therapeutic operation of the therapeutic member in response to a further operator's operation performed with the operating unit; and a control unit configured to control drive characteristics of the first and second drive units based on a bent state of the bendable section, wherein the medical instrument has a tubular portion which is moved by a force applied by the first drive unit;

the therapeutic member is connected to a distal end of the tubular portion;

the insertion tube has a tubular channel through which the tubular portion of the medical instrument is inserted so as to make the therapeutic member protrude from a distal end of the insertion tube; and the control unit comprises:
- operated-state detecting means for detecting the operator's operating state at the operating unit,
- bent-state detecting means for detecting the bent state of the bendable section,
- control means for controlling the drive characteristics of the first and second drive units in accordance with the operator's operating state detected by the operated-state detecting means, and
- correction means for correcting a driven state of at least one of the first and second drive units depending on the bent state of the bendable section detected by the bent-state detecting means;

wherein the correction means is configured to correct the force being applied to the tubular portion of the medical instrument by the first drive unit in accordance with the bent state of the bendable section detected by the bent-state detecting means such that the tubular portion is moved at a constant speed regardless of the bent state of the bendable section.

2. The endoscope system of claim 1, wherein:
the bent-state detecting means is configured to detect, as the bent state of the bendable section, an angular extent by which the bendable section is bent, and
the correction means is configured to correct the force being applied to the tubular portion in accordance with the detected bent state such that the tubular portion is moved at the constant speed regardless of the detected bent state.

3. The endoscope system of claim 1, wherein:
the bent-state detecting means is configured to detect, as the bent state of the bendable section, a direction in which the bendable section is bent, and
the correction means is configured to correct the force being applied to the tubular portion in accordance with the detected bent direction such that the tubular portion is moved at the constant speed regardless of the detected bent direction.

4. An endoscope system comprising:
an endoscope comprising an elongated flexible insertion tube having a distal end accommodating therein at least an imaging optical system and having a flexibly bendable section juxtaposed to the distal end, the insertion tube being inserted into an object being examined;
a medical instrument used in combination with the endoscope and inserted into the object through the insertion tube inserted into the object, the medical instrument having a therapeutic member that comprises an opening and closing portion that opens and closes;
an operating unit manually operated by an operator to command both an inserting and pulling-out operation of the medical instrument and a therapeutic operation of the therapeutic member of the medical instrument;
a first drive unit configured to drive the medical instrument to perform the inserting and pulling-out operation thereof in response to an operator's operation performed with the operating unit;
a second drive unit configured to drive the medical instrument to perform the therapeutic operation of the therapeutic member in response to a further operator's operation performed with the operating unit; and
a control unit configured to control drive characteristics of the first and second drive units based on a bent state of the bendable section,
wherein the medical instrument has a tubular portion which is moved by a force applied by the first drive unit;
the therapeutic member is connected to a distal end of the tubular portion;
the insertion tube has a tubular channel through which the tubular portion of the medical instrument is inserted so as to make the therapeutic member protrude from a distal end of the insertion tube; and
the control unit comprises;
- operated-state detecting means for detecting the operator's operating state at the operating unit,
- bent-state detecting means for detecting the bent state of the bendable section,
- control means for controlling the drive characteristics of the first and second drive units in accordance with the operator's operating state detected by the operated-state detecting means, and
- correction means for correcting a driven state of at least one of the first and second drive units depending on the bent state of the bendable section detected by the bent-state detecting means;

wherein the correction means is configured to correct an open/close state of the therapeutic member, which open/close state is under the drive of the second drive unit, in accordance with the bent state of the bendable section such that an open/close stroke of the therapeutic member is kept at a constant value regardless of the bent state of the bendable section.

5. An endoscope system comprising:
an endoscope comprising an elongated flexible insertion tube having a distal end accommodating therein at least an imaging optical system and having a flexibly bendable section juxtaposed to the distal end, the insertion tube being inserted into an object being examined;
a medical instrument used in combination with the endoscope and inserted into the object through the insertion tube inserted into the object, the medical instrument having a therapeutic member that comprises an opening and closing portion that opens and closes;
an operating unit manually operated by an operator to command both an inserting and pulling-out operation of the medical instrument and a therapeutic operation of the therapeutic member of the medical instrument;
a first drive unit configured to drive the medical instrument to perform the inserting and pulling-out operation thereof in response to an operator's operation performed with the operating unit;
a second drive unit configured to drive the medical instrument to perform the therapeutic operation of the therapeutic member in response to a further operator's operation performed with the operating unit; and
a control unit configured to control drive characteristics of the first and second drive units based on a bent state of the bendable section, wherein the medical instrument has a tubular portion which is moved by a force applied by the first drive unit;

the therapeutic member is connected to a distal end of the tubular portion;

the insertion tube has a tubular channel through which the tubular portion of the medical instrument is inserted so as to make the therapeutic member protrude from a distal end of the insertion tube; and the control unit comprises;

operated-state detecting means for detecting the operator's operating state at the operating unit, bent-state detecting means for detecting the bent state of the bendable section, control means for controlling the drive characteristics of the first and second drive units in accordance with the operator's operating state detected by the operated-state detecting means, and correction means for correcting a driven state of at least one of the first and second drive units depending on the bent state of the bendable section detected by the bent-state detecting means;

wherein the correction means is configured to correct wherein an open/close state of the therapeutic member, which open/close state is under the drive of the second drive unit, in accordance with the bent direction of the bendable section such that an open/close stroke of the therapeutic member is held at a constant value regardless of the bent direction of the bendable section.

\* \* \* \* \*

UNITED STATES PATENT AND TRADEMARK OFFICE
CERTIFICATE OF CORRECTION

| | | |
|---|---|---|
| PATENT NO. | : 7,998,058 B2 | Page 1 of 1 |
| APPLICATION NO. | : 11/529016 | |
| DATED | : August 16, 2011 | |
| INVENTOR(S) | : Yasuhito Kura et al. | |

It is certified that error appears in the above-identified patent and that said Letters Patent is hereby corrected as shown below:

Column 24, line 8 (claim 5) should read: an open/close state of the therapeutic member, Signed and Sealed this
Eighth Day of November, 2011

David J. Kappos
*Director of the United States Patent and Trademark Office*